(12) United States Patent
Hicks

(10) Patent No.: US 7,618,397 B2
(45) Date of Patent: Nov. 17, 2009

(54) FLUID DELIVERY SYSTEM WITH PUMP CASSETTE

(75) Inventor: Jeffrey H. Hicks, Jeannette, PA (US)

(73) Assignee: Medrad, Inc., Indianola, PA (US)

( * ) Notice: Subject to any disclaimer, the term of this patent is extended or adjusted under 35 U.S.C. 154(b) by 222 days.

(21) Appl. No.: 11/403,119

(22) Filed: Apr. 12, 2006

(65) Prior Publication Data

US 2007/0244435 A1    Oct. 18, 2007

(51) Int. Cl.
*A61M 1/00*    (2006.01)

(52) U.S. Cl. .................... 604/151; 604/500; 604/67; 604/131; 417/360

(58) Field of Classification Search ............ 604/30, 604/32, 35, 500, 506, 65, 67, 113, 114, 122, 604/123, 131, 149, 151, 153, 246, 248; 128/DIG. 12; 417/360, 205, 206
See application file for complete search history.

(56) References Cited

U.S. PATENT DOCUMENTS

| | | | |
|---|---|---|---|
| 4,641,522 A * | 2/1987 | Lopresti ...................... 73/261 |
| 5,460,609 A | 10/1995 | O'Donnell |
| 5,515,851 A | 5/1996 | Goldstein |
| 5,573,515 A | 11/1996 | Wilson et al. |
| 5,800,397 A | 9/1998 | Wilson et al. |
| 5,840,026 A | 11/1998 | Uber, III et al. |
| 5,916,165 A | 6/1999 | Duchon et al. |
| 6,063,052 A * | 5/2000 | Uber et al. ................... 604/32 |
| 6,385,483 B1 | 5/2002 | Uber, III et al. |
| 6,629,954 B1 | 10/2003 | Heruth |
| 6,641,562 B1 * | 11/2003 | Peterson ..................... 604/141 |
| 6,692,318 B2 | 2/2004 | McBride |
| 6,731,971 B2 * | 5/2004 | Evans et al. ................. 600/431 |
| 6,743,201 B1 | 6/2004 | Dönig et al. |

OTHER PUBLICATIONS

Internationlal Preliminary Report on Patentability for Counterpart PCT application No. PCT/US2007/66388, Mar. 12, 2009.
International Search Report and Written Opinion for Counterpart PCT application No. PCT/US2007/66388, Sep. 24, 2008.

* cited by examiner

*Primary Examiner*—Kevin C Sirmons
*Assistant Examiner*—Bhisma Mehta
(74) *Attorney, Agent, or Firm*—Jill Denesvich; James R. Stevenson

(57) ABSTRACT

The fluid delivery system includes a control console adapted to control delivery of fluid to a patient and a pump cassette disposed in a pump cassette socket in the control console and operatively controlled by the control console. The pump cassette includes a pump housing formed by opposing housing members that cooperatively define a pump chamber. A pair of meshed gears is disposed in the pump chamber and separate the pump chamber into a fluid inlet area and a fluid outlet area accessible through respective inlet and outlet ports in the pump housing. The gears are adapted to pressurize fluid for delivery to the patient. Other features of the system include a fluid heater upstream of the pump cassette, air detectors associated with the inlet and outlet ports of the pump cassette, and a sensor to read an encoding device associated with the pump cassette.

30 Claims, 16 Drawing Sheets

FLUID DELIVERY SYSTEM WITH PUMP CASSETTE

BACKGROUND OF THE INVENTION

1. Field of the Invention

The present invention relates to fluid delivery systems for supplying fluids to patients, for example, during medical diagnostic and therapeutic procedures and, further, to a fluid delivery system with a removable pumping section or pump cassette.

2. Description of Related Art

In many medical diagnostic and therapeutic procedures, a medical practitioner such as a physician injects a patient with a fluid. In recent years, a number of injector-actuated syringes and powered injectors for pressurized injection of fluids, such as contrast media, have been developed for use in procedures such as angiography, computed tomography ("CT"), ultrasound, and NMR/MRI. In general, these powered injectors are designed to deliver a preset amount of contrast media at a preset flow rate through the use of a removable and disposable syringe.

Angiography is used in the detection and treatment of abnormalities or restrictions in blood vessels. In an angiographic procedure, a radiographic image of a vascular structure is obtained through the use of a radiographic contrast medium, sometimes referred to simply as contrast, which is injected through a catheter. The vascular structures in which the contrast is injected are filled with contrast. X-rays are passed through the region of interest and are absorbed by the contrast, causing a radiographic outline or image of the blood vessels containing the contrast. The resulting images may be displayed on, for example, a video monitor and recorded.

In a typical angiographic procedure, the medical practitioner places a cardiac catheter into a vein or artery. The catheter is connected to either a manual or to an automatic contrast injection mechanism. A typical manual contrast injection mechanism includes a syringe in fluid connection with the catheter. The fluid path also includes, for example, a source of contrast, a source of flushing fluid, typically saline, and a pressure transducer to measure patient blood pressure. In a typical system, the source of contrast is connected to the fluid path via a valve, for example, a three-way stopcock. The source of saline and the pressure transducer may also be connected to the fluid path via additional valves. The operator of the manual system controls the syringe and each of the valves to draw saline or contrast into the syringe and to inject the contrast or saline into the patient through the catheter. The operator of the syringe may adjust the flow rate and volume of injection by altering the force applied to the plunger of the syringe. Manual sources of fluid pressure and flow used in these medical applications, such as syringes and manifolds, therefore require operator effort which provides feedback of the fluid pressure/flow generated to the operator. The feedback is desirable but the operator effort often leads to fatigue. Thus, fluid pressure and flow may vary depending on the operator's strength and technique.

Automatic contrast injection mechanisms typically include a syringe connected to a powered injector having, for example, a powered linear actuator. Typically, an operator enters settings into an electronic control system of the powered injector, for example, for a fixed volume of contrast and a fixed rate of injection. In many systems, there is no interactive control between the operator and the powered injector except to start or stop the injection. A change in flow rate in such systems occurs simply by stopping the machine and resetting the injection parameters. Automation of angiographic procedures using powered injectors is discussed, for example, in U.S. Pat. Nos. 5,460,609; 5,573,515; and 5,800,397.

U.S. Pat. No. 5,800,397 discloses an angiographic injector system having high pressure and low pressure systems. The high pressure system includes a motor-driven injector syringe pump to deliver radiographic contrast under high pressure to a catheter. The low pressure system includes, among other things, a pressure transducer to measure blood pressure and a pump to deliver a saline solution to the patient as well as to aspirate waste fluid. A manifold is connected to the syringe pump, the low-pressure system, and the patient catheter. A flow valve associated with the manifold is normally maintained in a first state connecting the low pressure system to the catheter through the manifold, and disconnecting the high pressure system from the catheter and the low pressure system. When pressure from the syringe pump reaches a predetermined level, the valve switches to a second state connecting the high pressure system/syringe pump to the catheter, while disconnecting the low pressure system from the catheter and from the high pressure system. Compliance in the system components, for example, expansion of the syringe, tubing, and other components under pressure may lead to a less than optimal injection bolus. Moreover, the arrangement of the system components of U.S. Pat. No. 5,800,397 results in relatively large amounts of wasted contrast and/or undesirable injection of an excessive amount of contrast.

The injector system of U.S. Pat. No. 5,800,397 also includes a handheld remote control connected to a console. The control includes saline push button switches and a flow rate control lever or trigger. By progressive squeezing of the control trigger, the user provides a command signal to the console to provide a continuously variable injection rate corresponding to the degree of depression of the control trigger. U.S. Pat. No. 5,916,165 discloses a handheld pneumatic controller for producing a variable control signal to control a rate of fluid dispersement to the patient in an angiographic system. U.S. Pat. No. 5,515,851 discloses an angiographic system with a finger-activated control pad to regulate the injection of fluids.

U.S. Pat. No. 5,840,026 discloses a fluid delivery system in which an electronic control system is connected to the fluid delivery system and a tactile feedback control unit. In one embodiment, the tactile feedback control unit includes a disposable syringe that is located within a durable/reusable cradle and is in fluid connection with the fluid being delivered to the patient. The cradle is electrically connected to the electronic control system and is physically connected to a sliding potentiometer that is driven by the plunger of a disposable syringe. During use of the fluid delivery system of U.S. Pat. No. 5,840,026, the operator holds the cradle and syringe and, as the operator depresses the sliding potentiometer/syringe plunger assembly, the plunger is moved forward displacing fluid toward the patient and creating pressure in the syringe. The sliding potentiometer tracks the position of the syringe plunger. The electronic control system controls the amount of fluid injected into the patient based on the change in position of the syringe plunger. As the fluid is injected, the pressure the operator feels in his or her hand is proportional to the actual pressure produced by the system. The force required to move the syringe plunger provides the operator with tactile feedback of pressure in the system. The operator is able to use this feedback to ensure the safety of the injection procedure. Unlike the case of a manual system, the system of U.S. Pat. No. 5,840,026 does not require the operator to develop the system pressure and flow rate. The operator develops a smaller, manually applied pressure that corresponds to or is proportional to the system pressure.

In certain medical fluid delivery applications it is desirable to deliver tightly controlled volumes of fluid at generally uniform/continuous pressure without pressure pulsations that can cause variations in fluid flow rate. In each of the systems discussed hereinabove, a positive-displacement injector with a piston is used to actuate a plunger disposed within a disposable syringe to alternately fill and dispense fluid from the syringe. During an injection procedure, the injector piston engages the syringe plunger to dispense fluid from the syringe. The movement of the engaged piston and syringe plunger often creates pressure pulsations during the positive displacement stroke of the injector piston thereby resulting in variations in fluid flow delivered to the patient from the syringe. Thus, the pressure profiles provided by such syringe injector systems do not deliver desired "uniform" pressure profiles often required in certain fluid injection procedures, such as where a continuous flow of fluid at a generally uniform or continuous pressure is desired. Moreover, this type of system is inherently incapable of providing a true continuous flow of fluid as the volume of injectable fluid is limited by the volume of the syringe used with the injector.

SUMMARY OF THE INVENTION

In one aspect, the invention is directed to a pump cassette for delivering fluids to patient. The pump cassette generally comprises a pump housing formed by a first housing member and a second housing member which cooperatively defining an enclosed pump chamber with an interior wall. The pump cassette generally further comprises at least a pair of meshed gears disposed in the pump chamber and separating the pump chamber into a fluid inlet area and a fluid outlet area accessible through respective inlet and outlet ports in the pump housing. The gears are adapted to pressurize fluid for delivery to the patient.

The gears may contact the interior wall of the pump chamber over at least a portion of their periphery. In one particular form, the meshed gears are spur gears. The meshed gears may be composite structures each comprising a substantially rigid gear core and a resiliently deformable radial casing disposed about the gear core.

The inlet and outlet ports in the pump housing may be formed or provided as luer connectors. The first and second housing members may be formed substantially identically such that opposing sides of the pump housing are substantially identical. An encoding device may be associated with the pump housing and be operable to provide pump cassette information to a sensor. In one form, the encoding device may be an optically readable device such as a bar code. The pump cassette information may include, but is not intended to be limited to, pump cassette sizing information, pump cassette flow rate information, and pump cassette manufacturing information.

The meshed gears may be resiliently deformable at least at their outer periphery. In the pump cassette, the spacing between gear teeth on each gear may be sized to conduct a predetermined amount of fluid about the periphery of the gear along the interior wall of the pump chamber.

Another aspect of the invention is directed to a fluid delivery system incorporating, generally, a control console and a pump cassette connected to and operated by the control console for delivering fluid to a patient. The pump cassette generally comprises a pump housing formed by a first housing member and a second housing member which cooperatively define an enclosed pump chamber with an interior wall. The pump cassette generally further comprises at least a pair of meshed gears disposed in the pump chamber and separating the pump chamber into a fluid inlet area and a fluid outlet area accessible through respective inlet and outlet ports in the pump housing. The gears are adapted to pressurize fluid for delivery to the patient.

The pump cassette may be disposed in a pump cassette socket in the control console. A fluid heater may be located upstream of the pump cassette on the control console to provide heated fluid to the pump chamber. An air detector may also be provided on the control console and be associated with the inlet port and/or outlet port of the pump housing to monitor the inlet port and/or outlet port for the presence of air bubbles.

The control console may comprise a sensor adapted to detect an encoding device associated with the pump housing and operable to provide pump cassette information to the sensor. The encoding device may comprise an optically readable device such as a bar code. The pump cassette information may include, but is not intended to be limited to, pump cassette sizing information, pump cassette flow rate information, and pump cassette manufacturing information.

The gears may contact the interior wall of the pump chamber over at least a portion of their periphery. In one particular form, the meshed gears are spur gears. The meshed gears may be composite structures each comprising a substantially rigid gear core and a resiliently deformable radial casing disposed about the gear core.

The inlet and outlet ports in the pump housing may be formed or provided as luer connectors. The first and second housing members may be formed substantially identically such that opposing sides of the pump housing are substantially identical.

The meshed gears may be resiliently deformable at least at their outer periphery. In the pump cassette, the spacing between gear teeth on each gear may be sized to conduct a predetermined amount of fluid about the periphery of the gear along the interior wall of the pump chamber.

A further aspect of the invention relates to a method of preparing a fluid delivery system to provide fluid to a patient, generally comprising providing a control console adapted to control delivery of fluid to the patient, operatively associating a pump cassette with the control console, with the control console adapted to control operation of the pump cassette for delivering fluid to the patient, and placing the pump chamber of the pump cassette in fluid communication with a source of fluid to be delivered to the patient.

The method may further comprise heating the fluid upstream of the pump cassette and monitoring the inlet port and/or outlet port to the pump chamber for the presence of air bubbles. An encoding device on the pump housing of the pump cassette may be sense with a sensor on the control console. The encoding device is desirably adapted to provide pump cassette information to the sensor. As an example, the encoding device may be optically sensed and in one particular form may be a bar code.

The control console may control operation of the pump cassette based on the pump cassette information sensed from the encoding device. The method may further comprise connecting the control console to a user interface device adapted to input one or more fluid delivery parameters to the control console. Such a user interface device may be further adapted to control operation of the pump cassette upon actuation. As examples, the user interface may be a handcontroller, actuating button, touch-screen display, or other similar control device.

Further details and advantages of the invention will become clear upon reading the following detailed description in conjunction with the accompanying drawing figures, wherein like parts are identified with like reference numerals throughout.

DESCRIPTION OF THE PREFERRED EMBODIMENTS

For purposes of the description hereinafter, spatial orientation terms, if used, shall relate to an embodiment of the invention as it is oriented in the accompanying drawing figures or otherwise described in the following description of the invention. However, it is to be understood that the invention embodiments described hereinafter may assume many alternative variations and configuration. It is also to be understood that the specific devices illustrated in the accompanying drawing figures and described herein are simply exemplary to the invention and should not be considered as limiting.

The invention described herein, in one embodiment, relates to a fluid delivery system suitable for the delivery of medical fluid(s) to a patient. The system may be adapted to supply a relatively small volume of fluid to a patient making the system suitable for use as a drug infusion, gene therapy, or chemotherapy delivery vehicle, or a larger volume of fluid such as contrast media used during computed tomography ("CT") procedures. In either exemplary situation, the fluid delivery system is capable of delivering highly accurate (small or large) volumes of fluid at relatively constant or uniform pressures. Such pressures may be low in the case of drug delivery, gene therapy, or chemotherapy applications, moderate in the case of a CT application, or relatively high (i.e., up to about 2000 PSI) in the case of cardiovascular angiography applications ("CV" applications). In one particular form, the fluid delivery system includes a control console and a removable and desirably disposable pump cassette. The control console controls operation of the pump cassette to conduct a fluid injection procedure on a patient. The pump cassette desirably includes at least a pair of meshed gears that are adapted to deliver substantially uniform fluid pressure and controlled and highly accurate volumes of fluid to a patient via a patient interface device which typically includes devices such as catheters or intravenous ("IV") needle cannulas and transfusion sets including such IV needle cannulas.

Figure 1:
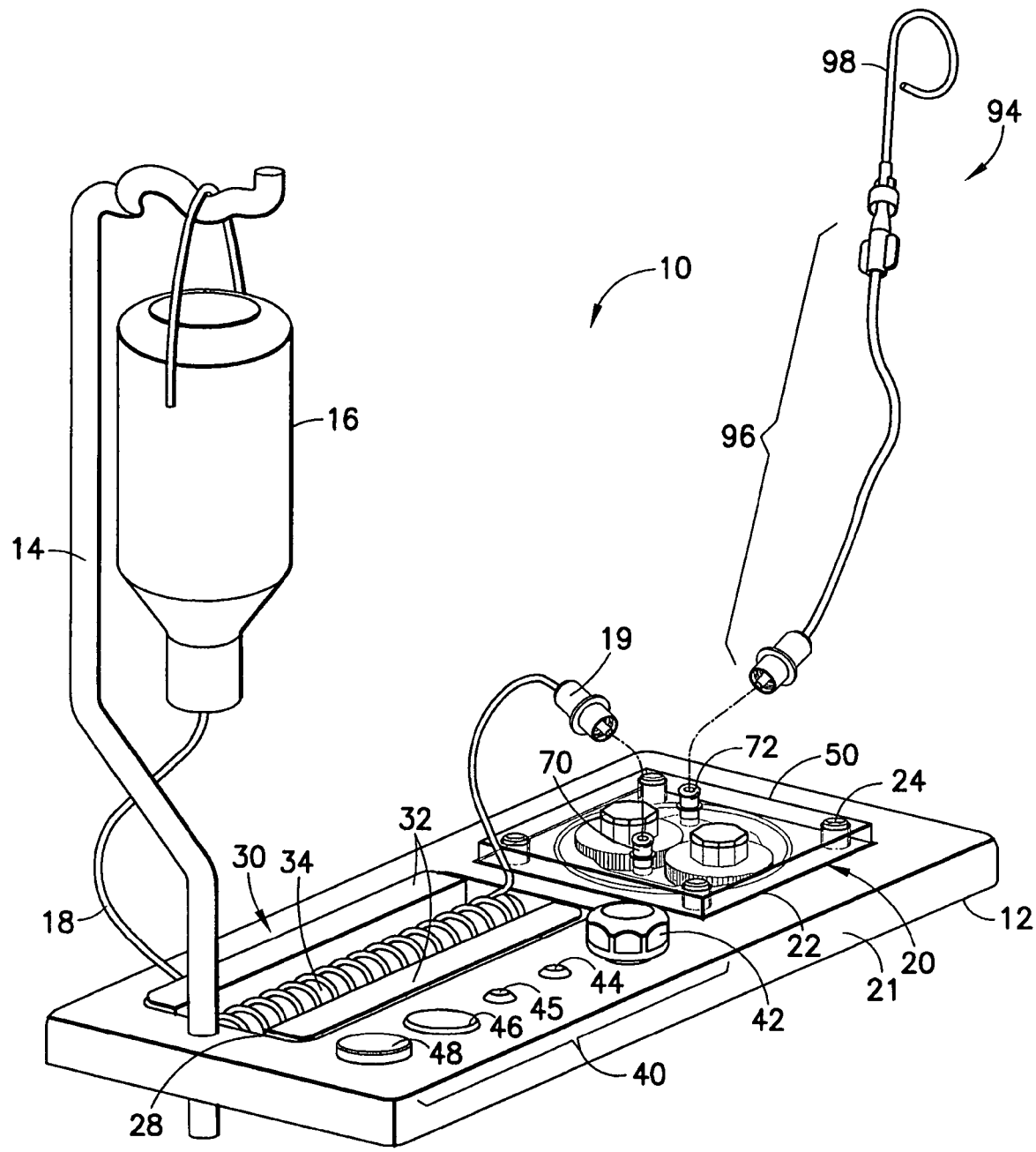
FIG. 1 is a perspective view of an embodiment of a fluid delivery system generally including a control console and a removable pump cassette.

FIG. 1 shows an embodiment of the invention. FIG. 1 shows a fluid delivery system 10 (hereinafter "system 10") that generally includes a control console 12 and a pump cassette 50 operatively associated will, and controlled by control console 12. Control console 12 controls operation of pump cassette 50 for conducting fluid delivery/injection procedures on a patient. Generally, control console 12 includes a pump cassette interface section 20, a fluid heating section 30, and an operator control section 40, all of which are discussed in detail herein. Pump cassette 50 is operatively associated with control console 12 by interfacing with the pump cassette interface section 20 on control console 12. Control console 12 further includes a support 14 for supporting a supply of medical fluid 16, typically a bottle or IV bag, containing the medical fluid that is to be delivered to a patient via a patient interface device or section 94 described further herein. Examples of medical fluid 16 that may be used in system 10 include contrast media in the case of CT and CV procedures, liquid drugs used in gene therapy and chemotherapy procedures, and, further, to more common liquids supplied to patients on a regular basis in medical settings such as saline and glucose solutions. Medical tubing 18 connects medical fluid source 16 with pump cassette 50 as described herein and terminates at a distal end with a luer connector 19.

Figure 2:
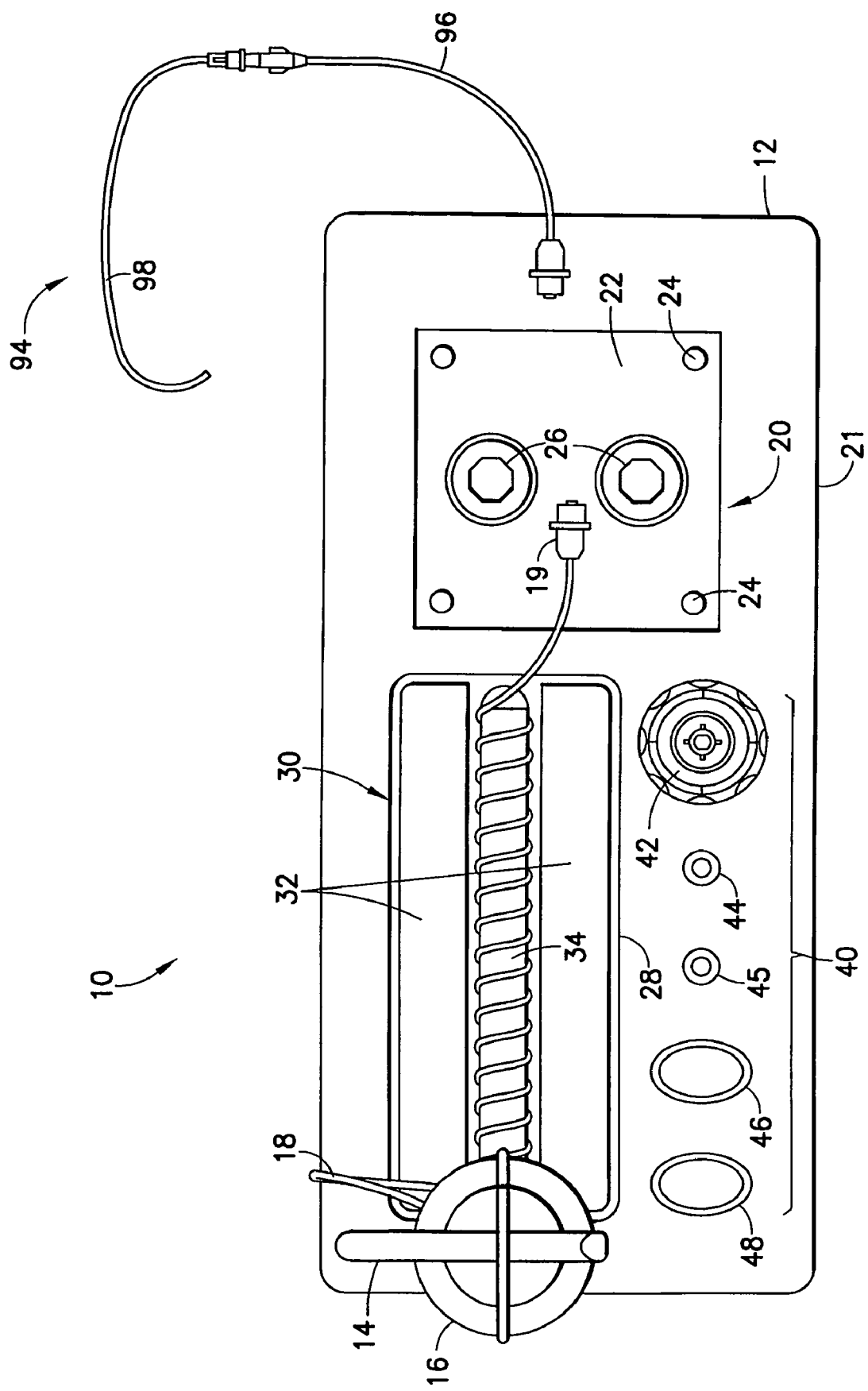
FIG. 2 is a top view of the fluid delivery system of FIG. 1.
Figure 3:
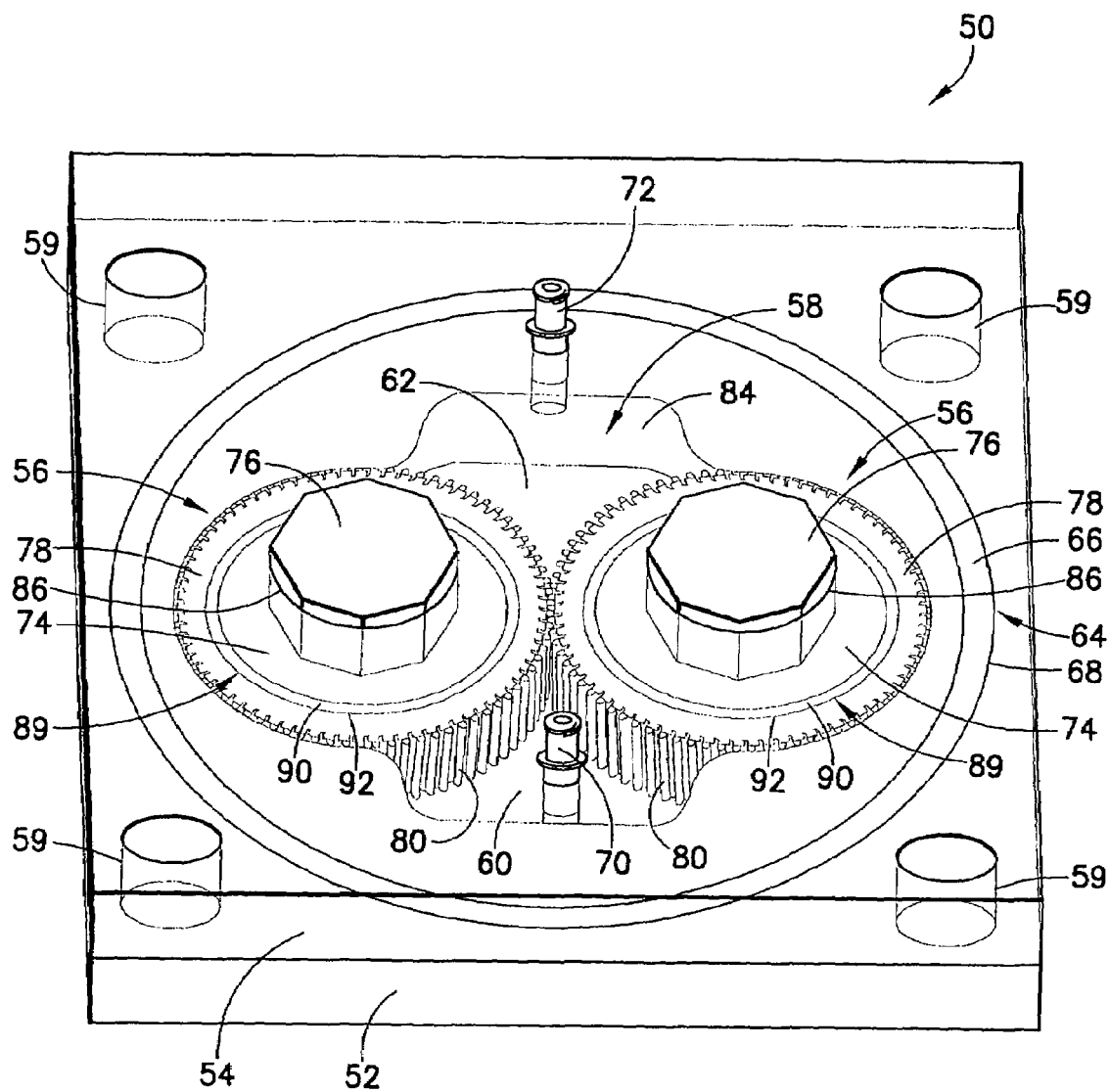
FIG. 3 is a perspective view of a pump cassette used in the fluid delivery system of FIG. 1.

Referring further to FIGS. 1-6, pump cassette 50 is adapted to interact with the pump cassette interface section 20 of control console 12 to operatively associate the pump cassette 50 with the control console 12. Pump cassette 50 is intentionally omitted from FIG. 2 to allow a complete viewing of pump cassette interface section 20 of control console 12. Pump cassette 50 is desirably a disposable composite structure that is adapted for removable association with the pump cassette interface section 20 of control console 12. Control console 12 comprises a housing or body structure 21 which forms the support structure for the components of the pump cassette interface section 20, fluid heating section 30, and operator control section 40. In one form, pump cassette interface section 20 comprises a recessed area or socket 22 defined in control console body 21 which is sized to accept pump cassette 50 therein. A series of pins 24, or at least a singular pin 24, may project upward from pump cassette socket 22 to engage pump cassette 50 to connect and secure the pump cassette 50 to the control console body 21. Pump cassette 50 is configured to accept pins 24 to removably connect pump cassette 50 with control console 12. For example, pump cassette 50 may be formed with openings adapted to cooperate with pins 24 in a friction fit manner to connect the pump cassette 50 with the control console 12, as described further herein. Pump cassette interface section 20 is further adapted to drive gearing provided within pump cassette 50, as also described herein. This adaptation takes the form of drive elements 26 which are used to drive the gearing disposed within pump cassette 50. As examples, drive elements 26 may be protruding drive shafts adapted to engage corresponding openings in the gearing in pump cassette 50 to drive such gearing, or may be drive bosses recessed within pump cassette socket 22 and which are adapted to accept mating protrusions depending from the gearing in pump cassette 50. Drive elements 26 may take any convenient shape or configuration, such rectangular or triangular (i.e., polygonal), circular with a protruding pin or spline, or another suitable shape such as generally oval-shaped. In the drive boss configuration, drive elements 26 may be openings or recesses of any suitable shape such as polygonal, circular with a groove for accepting a pin or spline, or oval and like non-polygonal shapes. Control console body 21 is further formed with an open typically recessed area or space 28 which is adapted to accept heating elements and other components forming the fluid heating section 30 on control console 12 as discussed herein. In FIG. 2, drive elements 26 are illustrated in the drive boss configuration adapted to accept mating protrusions from the gearing in pump cassette 50, as described herein.

As indicated, pump cassette 50 is desirably a composite structure and made of relatively inexpensive materials and by well-known manufacturing techniques so that the pump cassette 50 may disposed of after a preset number of fluid delivery/injection procedures have been accomplished using the pump cassette 50. Generally, pump cassette 50 comprises a base or first housing member 52 and a cover or second housing member 54. Each of these members 52, 54 are formed of molded plastic material and are desirably transparent or slightly opaque. At least a pair of gears 56 is disposed between first housing member 52 and second housing member 54. In the illustrated embodiment, first housing member 52 is adapted to interface with control console 12 and, in particular, the pump cassette interface section 20 on the control console 12. First housing member 52 is a generally rigid plate-shaped structure that defines a recessed area which defines a pump chamber 58 within pump cassette 50. First housing member 52 further defines a plurality of cylindrical bores 59 at each of its four corners which are adapted to accept pins 24 projecting upward within pump cassette socket 22 in pump cassette interface section 20 on control console 12 to secure the pump cassette 50 to the control console body 21. Pins 24 may be inserted into cylindrical bores 59 and may be held in the bores 59 via a friction fit connection to removably secure pump cassette 50 to control console body 21 and thus associate the pump cassette with control console 12.

Gears 56 are disposed in pump chamber 58 such that the gears 56 are in conventional meshed engagement within the pump chamber 58. The meshed engagement of gears 56 within pump chamber 58 has the effect of dividing or separating the pump chamber 58 into two portions or areas, termed for convenience hereinafter as a fluid inlet area 60 and a fluid outlet area 62. However, these specific terms should not be read as limiting the operational characteristics of pump cassette 50 in particular and system 10 in general. As described herein, gears 56 may optionally be operated in "reverse" whereby the fluid outlet area 62 functions as a "fluid inlet area" and the fluid inlet area 60 functions as a "fluid outlet area". Nonetheless, the usual operation of pump cassette 50 has gears 56 operating such that fluid from medical fluid source 16 enters fluid inlet area 60 at a low pressure and is pressurized by rotating gears 56 to a higher pressure at the fluid outlet area 62 and delivered to a patient via patient interface device or section 94 fluidly connected to the fluid outlet area 62.

As indicated previously, in the present embodiment, base or first housing member 52 defines pump chamber 58 which receives gears 56, with second housing member 54 maintaining gears 56 disposed within the pump chamber 58. Thus, second housing member 54 acts as a cover to first housing member or base member 52. In particular, second housing member 54 covers and seals pump chamber 58 such that pump chamber 58 is a generally fluid tight chamber which houses gears 56. As an example, second housing member 54 may be adhesively sealed to first housing member 52 peripherally around pump chamber 58, such as with a suitable medical grade adhesive. Such an adhesive seal between first housing member 52 and second housing member 54 may be sufficient to provide a generally fluid-tight connection between the first housing member 52 and second housing member 54 thereby forming a generally fluid-tight and enclosed pump chamber 58 between the first and second housing members 52, 54 housing gears 56. However, to ensure that a fluid tight seal is maintained between first and second housing members 52, 54, a perimeter seal 64 may be provided which extends peripherally around pump chamber 58. Such a perimeter seal 64 may be formed by an O-ring 66 disposed within a perimetrical groove 68 extending around pump chamber 58 radially outward from pump chamber 58. O-ring 66 forms a generally fluid tight barrier between the first and second housing members 52, 54 when the cover or second housing member 54 is secured to the base or first housing member 52. While an adhesive connection is disclosed as a means of securing second housing member 54 to first housing member 52, other methods of securing the connection between the second housing member 54 and first housing member 52 may be used in place of an adhesive. Examples of such alternative methods include a simple mechanical clamping connection between second housing member 54 and first housing member 52 or by use of mechanical fasteners connecting second housing member 54 and first housing member 52. In such mechanical connections, O-ring 66 is desirably used to provide a generally fluid-tight seal around pump chamber 58 thereby sealing pump chamber 58 from the external environment.

As shown in currently referenced FIGS. 1-6, an inlet port 70 is provided in second housing member 54 for connecting the fluid inlet area 60 of pump chamber 58 with medical tubing 18 used to connect the medical fluid source 16 with pump cassette 50. Similarly, an outlet port 72 is provided in second housing member 54 for connecting the fluid outlet area 62 of pump chamber 58 with patient interface device or section 94, discussed herein. As indicated previously, patient interface device 94 is used to fluidly connect pump cassette 50 intravenously with a patient. Inlet port 70 and outlet port 72 are shown as conventional or standard female luer connectors with an externally-threaded flange for engaging a suitable mating male luer connector on patient interface device 94.

Gears 56 are identical composite structures that are adapted to mesh or engage within pump chamber 58. One or both of gears 56 may be driven by drive elements 26 within the pump cassette socket 22 of the pump cassette interface section 20 on control console 12. Typically, only one of gears 56 is driven, with the second and additional gears 56, if present, operating as idler gears. If both gears 56 are driven, the gears 56 operate as a counter-rotating gear pair. Gears 56 are typically spur gears and each comprise a substantially rigid core 74. Each gear core 74 may be made of metal or molded plastic material and is adapted to engage a drive element 26 within the pump cassette socket 22 of pump cassette interface section 20 on control console 12. Each gear core 74 is formed with one or more drive element interface structures 76 adapted to engage one of the drive elements 26 within the pump cassette socket 22 of the pump cassette interface section 20. A radial casing 78 is desirably overmolded onto the gear core 74 thereby making each gear 56 a composite structure. Radial casing 78 is molded with gear teeth 80 that are adapted to mesh with the gear teeth 80 on the opposing gear 56 in pump chamber 58. While gear teeth 80 are illustrated as straight spur gear teeth with generally rounded tips or ends, the gear teeth 80 may also be formed with beveled or tapered tips or even blunted or planar tips. Moreover, gear teeth 80 may also be beveled or herringbone shaped gear teeth.

Figure 4:
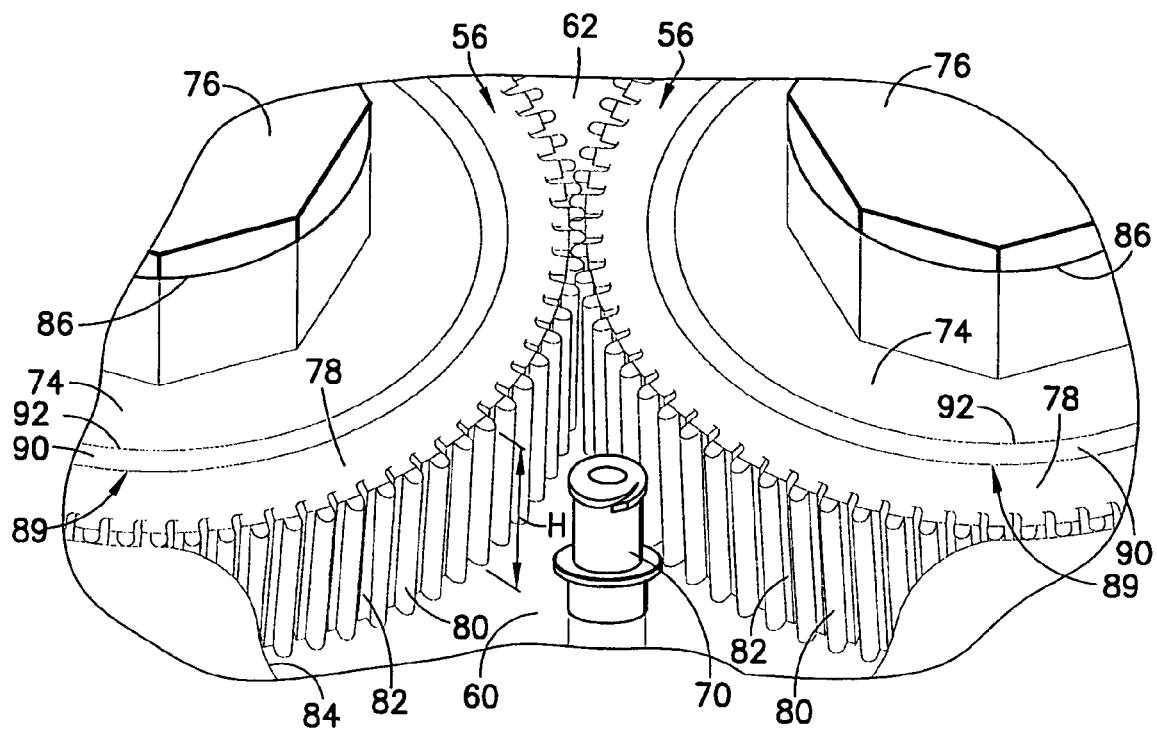
FIG. 4 is a close-up perspective view of the pump cassette of FIG. 3 showing meshed gears of the pump cassette.
Figure 5:
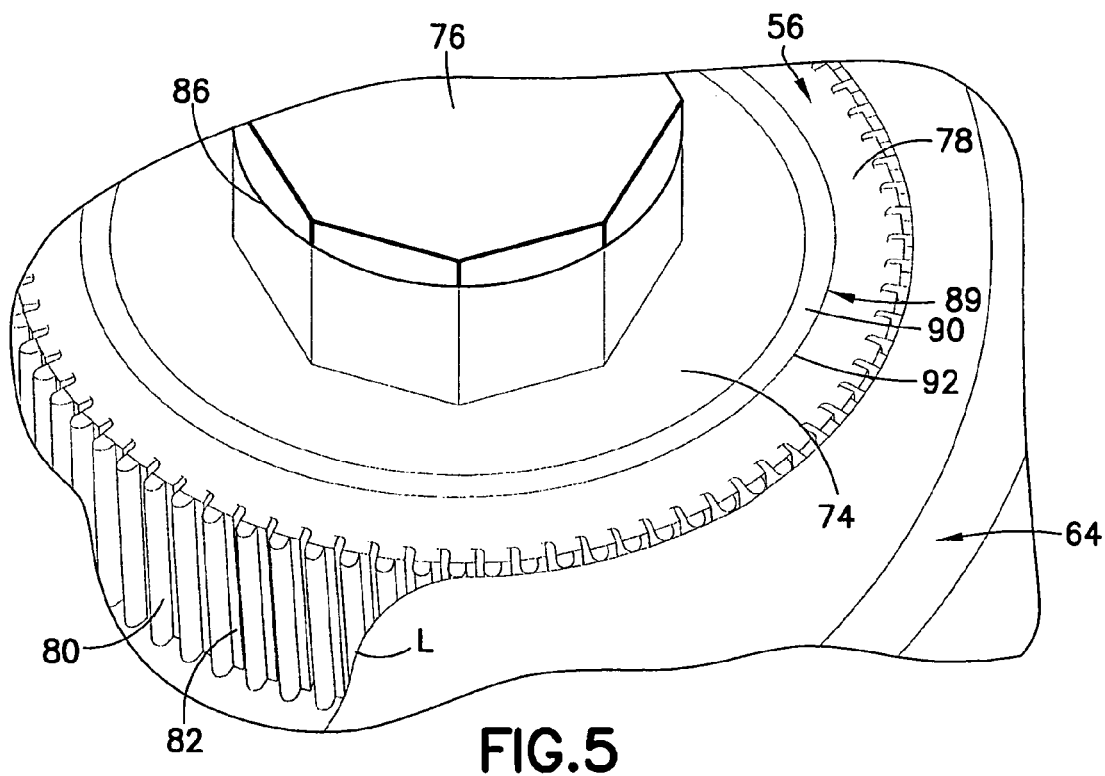
FIG. 5 is a close-up perspective view of one of the gears of the pump cassette of FIG. 3.

In one desirable embodiment, radial casing 78 is made of silicone rubber or a similar material. The resiliently flexible nature of silicone rubber and like materials is used to account for molding variances of the gear teeth 80 on radial casing 78 which is an inherent result of the overmolding process. Additionally, using a resiliently flexible material such as silicone rubber for radial casing 78 allows for inter-fitting interference engagement between the gear teeth 80 on opposing gears 56. Silicone rubber also has some inherent lubricating properties thereby making the meshed operation of gears 56 smoother and quieter. As illustrated in FIGS. 4 and 5 in particular, the gear teeth 80 on radial casing 78 define voids or spacing 82 therebetween. The resilient nature of the silicon rubber gear teeth 80 allows the gear teeth 80 to resiliently compress against an internal wall 84 of pump chamber 58 as gears 56 rotate within pump chamber 58 thereby sealing voids 82 along internal wall 84. Internal wall 84 defines a smooth lead-in curve L to prevent excessive wear of gear teeth 84 during operation of gears 56.

Figure 10:
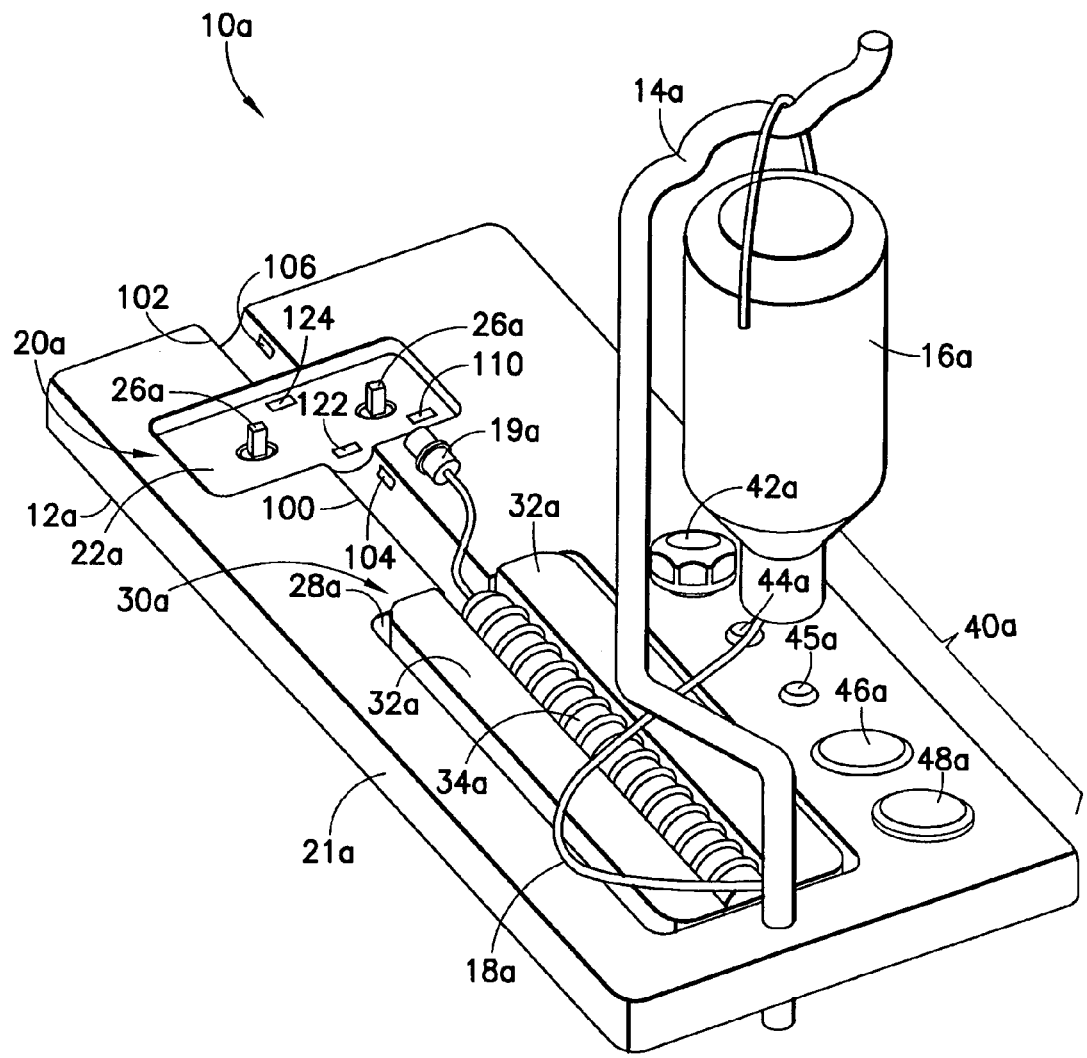
FIG. 10 is a perspective view of the fluid delivery system of FIG. 8 with the pump cassette removed from the control console.
Figure 11:
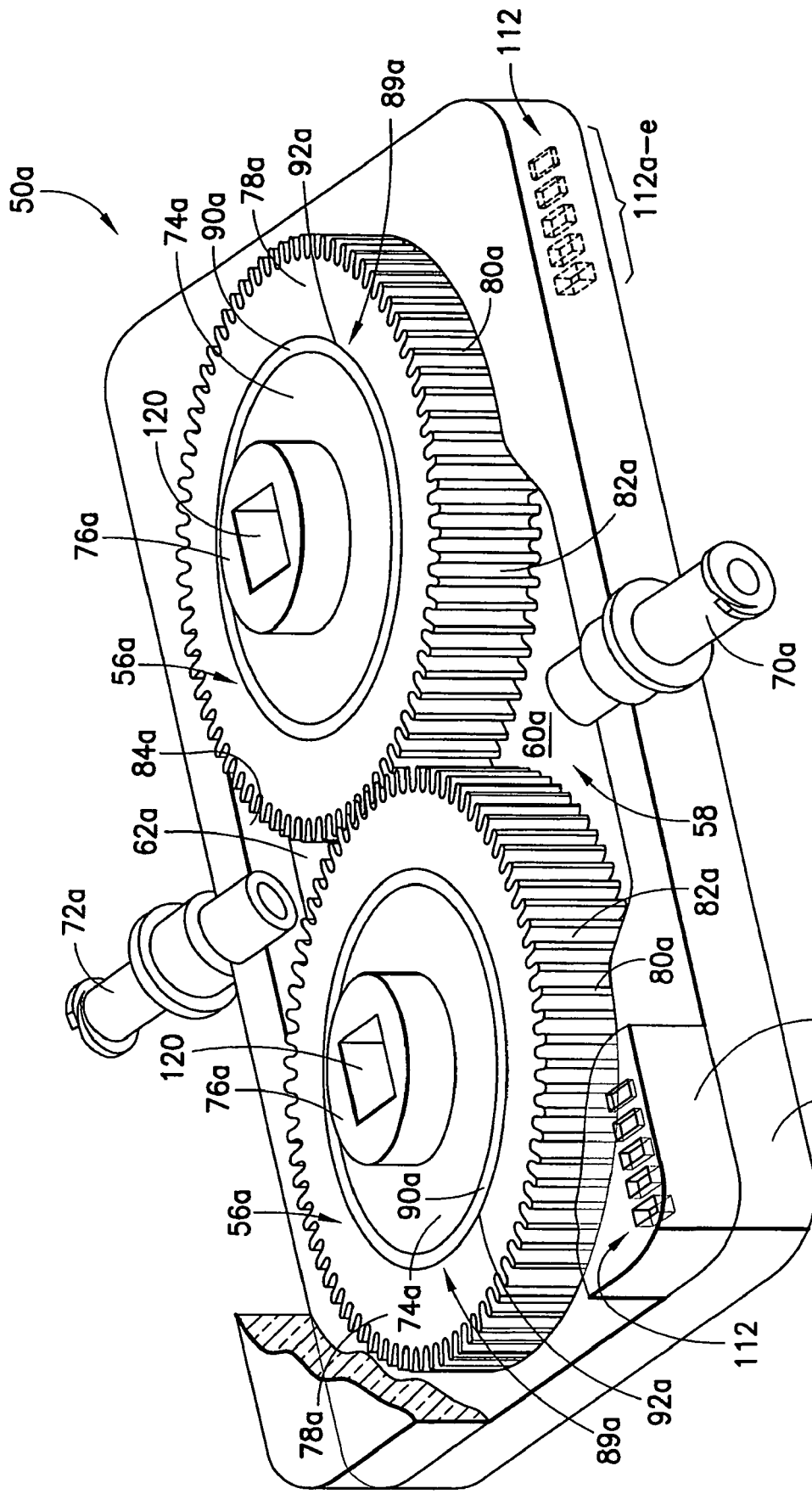
FIG. 11 is perspective view of a pump cassette adapted for use in the fluid delivery system of FIG. 8.
Figure 12:
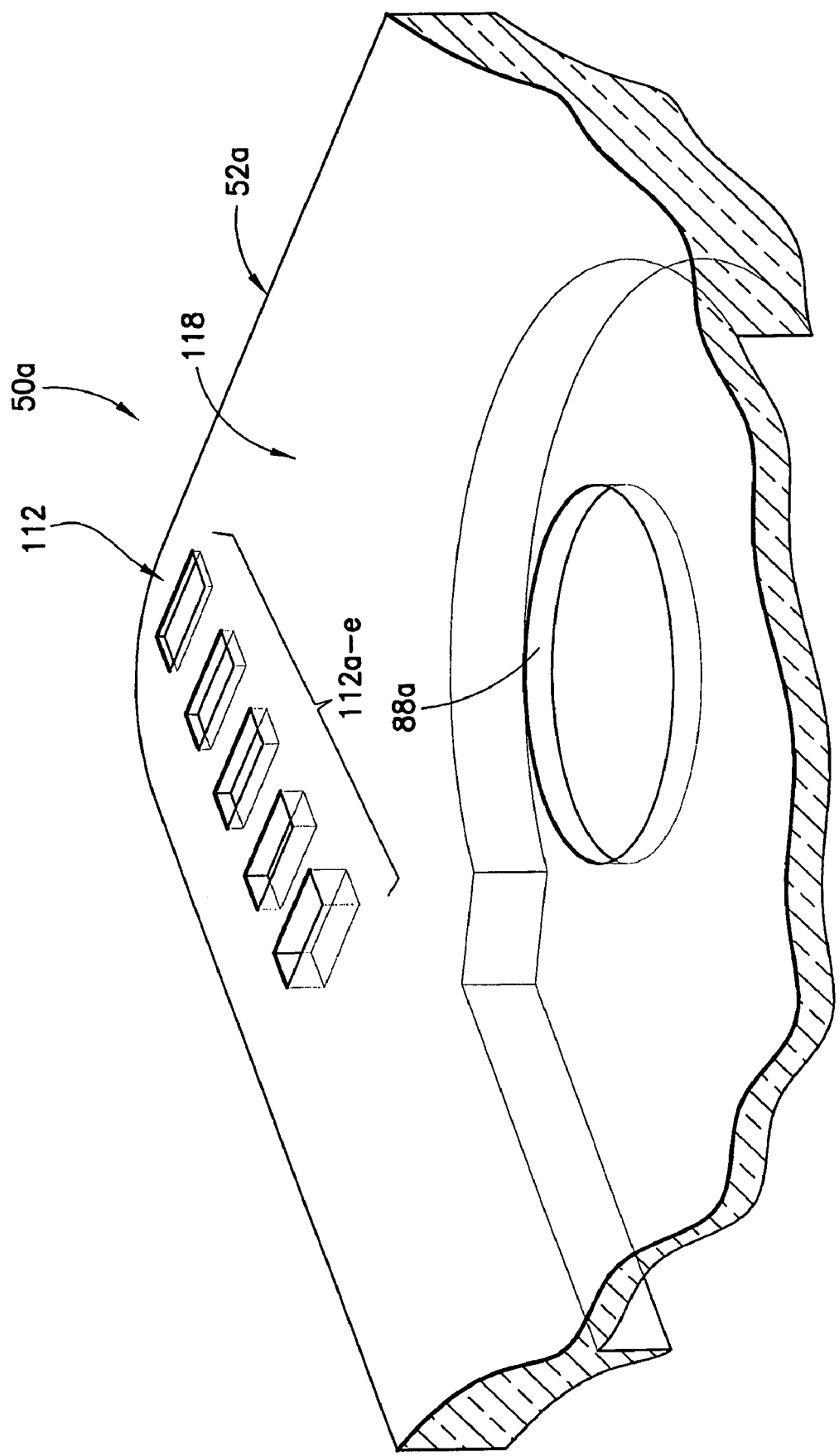
FIG. 12 is a detail view of a portion of the housing of the pump cassette of FIG. 11.

As indicated previously, one or both gears 56 are rotated by drive elements 26 through the engagement of drive element interfaces 76 on gear cores 74 with drive elements 26. The drive element interfaces 76 are adapted, for example, to be inserted into drive element "sockets" 26, as represented in FIG. 2, or to positively receive "protruding" drive elements 26*a* as represented in FIG. 10 discussed herein. In FIGS. 1-6, gears 56 are formed with protruding drive element interfaces 76 projecting from gear cores 74 and are, therefore, adapted to engage socket-type drive elements 26 in pump cassette socket 22 formed in the control console body 21 and generally forming the pump cassette interface section 20 on control console 20. To expedite manufacturing, gear cores 74 are desirably symmetrically formed with identical top and bottom-extending drive element interfaces 76. In the illustrated embodiment, drive element interfaces 76 are polygonal-shaped protrusions which are adapted to engage socket drive elements 26. In FIGS. 1-6 only the "top" drive elements interfaces 76 are shown, but it will be appreciated that the bottom side or end of each gear core 74 will include an identical depending drive element interface 76 which is inserted into one of the socket drive elements 26 in pump cassette socket 22. Referring briefly to FIGS. 14A-14E, examples of such depending drive element interfaces 76*a* are shown with respect to another embodiment of system 10*a*.

Figure 13:
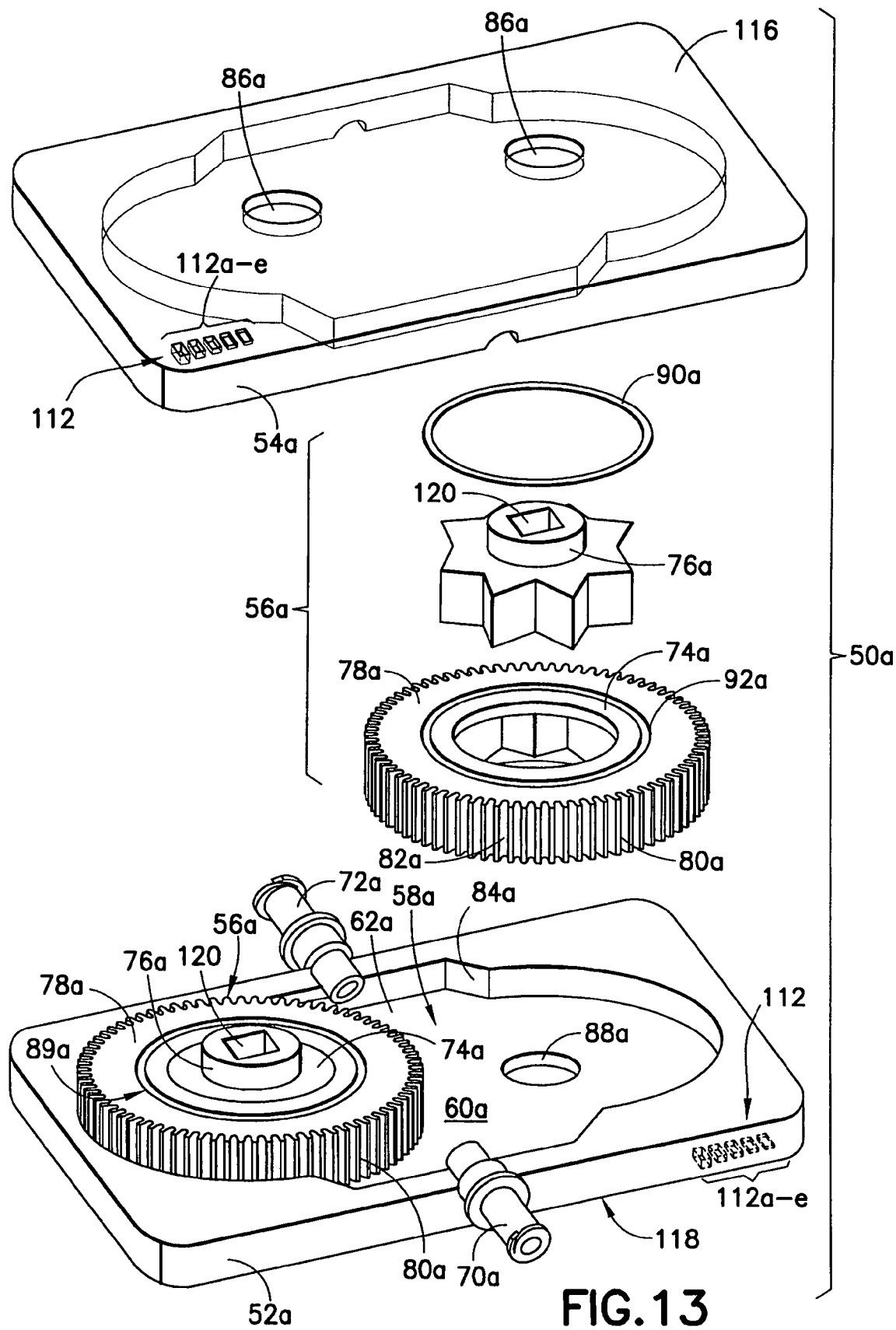
FIG. 13 is an exploded perspective view of the pump cassette of FIG. 11.

To accommodate the top and bottom extending drive element interfaces 76 extending from gear cores 74 of each gear 56, first housing member 52 and second housing member 54 each define pair of openings 86, 88*a* to allow the passage of the drive element interfaces 76 through the first and second housing members 52, 54. The openings 88*a* in second housing member (See FIG. 13) allows the bottom drive element interfaces 76 depending from gear cores 74 of gears 56 to engage the respective drive elements 26 within the pump cassette socket 22 of the pump cassette interface section 20 on control console 12. To ensure that pump chamber 58 remains fluidly sealed during operation of gears 56, each gear 56 includes top and bottom gear seals 89 which are similar to perimeter seal 64 discussed previously. In FIGS. 1-6, only the "top" gear seal 89 is shown. Gear seals 89 are each comprised of an O-ring 90 disposed in a groove 92 defined in each gear core 74 in a similar manner to the structure of perimeter seal 64, and as best illustrated in FIG. 13 discussed herein. Thus, O-rings 90 are disposed in respective perimetrical grooves 92 extending around drive element interfaces 76 on the top and bottom ends or sides of gear cores 74 of gears 56. As illustrated, the O-ring 90 of each "top" gear seal 89 on each gear core 76 is sandwiched between the cover or second housing member 54 and the gear core 74 to fluidly seal top openings 86 from pump chamber 58. A similar arrangement is found at the "bottom" gear seal 89 where the O-ring 90 of each "bottom" gear seal 89 on each gear core 74 is sandwiched between the base or first housing member 52 and the gear core 74 to seal bottom openings 88*a* (See FIG. 13) from pump chamber 58. However, it will be appreciated that the top and bottom gear seals 89 do not prevent gears 56 from rotating within pump chamber 58. It will further be appreciated that radial casing 78 about each gear core 74 may be formed and adapted to provide the desired fluid seal about the top and bottom extending drive element interfaces 76 on each gear 56.

One distinct feature of the pump cassette 50 is that gears 56 may be designed such that the voids or spacing 82 between each gear tooth 80 formed on radial casing 78 of each gear 56 may be designed to transport a preselected or predetermined volume of fluid so that one complete revolution of each gear 56 delivers a set volume of fluid to outlet port 72 of pump cassette 50. As an example, if radial casing 78 on each gear 56 is formed with seventy-seven gear teeth 80 and the void or spacing 82 between each gear tooth 80 is sized to accommodate one milliliter of fluid, then one complete revolution of such a gear 56 will deliver 153 milliliters of fluid to outlet port 72. The volume of fluid that may be accommodated by each void or spacing 82 between gear teeth 80 and, thus, the volume of fluid delivered per rotation of each gear 56 may be increased or decreased by changing a height or thickness H of each gear core 74 and by extension the radial casing 78 about the gear core 74. Thus, for the same rotation rate a "thicker" gear 56 with a gear core 74 of increased thickness H will deliver more liquid per rotation than a "thinner" gear 56 with a thinner gear core 74. As an alternative, the "thinner" gear 56 may be operated to deliver the same amount of fluid as the "thicker" gear 56 if the "thinner" gear 56 is rotated at a faster rate than the "thicker" gear 56. This latter operational control of gears 56 may be accomplished by controlling the rotational speed of drive elements 26 on control console 12.

The operational control of drive elements 26 of the pump cassette interface section 20 on control console 12 and, hence, operation control of gears 56 and the sizing of the gears 56 allows system 10 to be customized to support different fluid delivery/injection operations. For example, in a typical CT procedure it is generally desired to supply large volumes of contrast media at moderate pressures, on the order of 200-300 PSI. As a result, larger gears 56 (i.e., having gear cores 74 of greater thickness H) driven at moderate rotational speeds, for example, 4 RPM, are preferred. In contrast, in CV applications, such as angiography, smaller gears 56 (i.e., having gear cores 74 of smaller thickness H) driven at higher rotational speeds are preferred, thereby delivering smaller volumes of contrast media at higher pressures, for example, on the order of 1200 PSI. In system 10, pump cassette 50 may be customized to the meet the requirements of the fluid delivery/injection procedure through the appropriate sizing of gears 56 and the controlled operation of gears 56 by control console 12. Controlled operation of gears 56 may be accomplished by changing the motor speed of a drive motor driving one or both drive elements 26 of the pump cassette interface section 20 on control console 12. Pump cassette 50 operates generally as a positive displacement gear pump and is capable of delivering accurate volumes of fluid at substantially uniform pressures without or with a minimum of pressure pulsations that are common in syringe-type injectors discussed previously.

Figure 6:
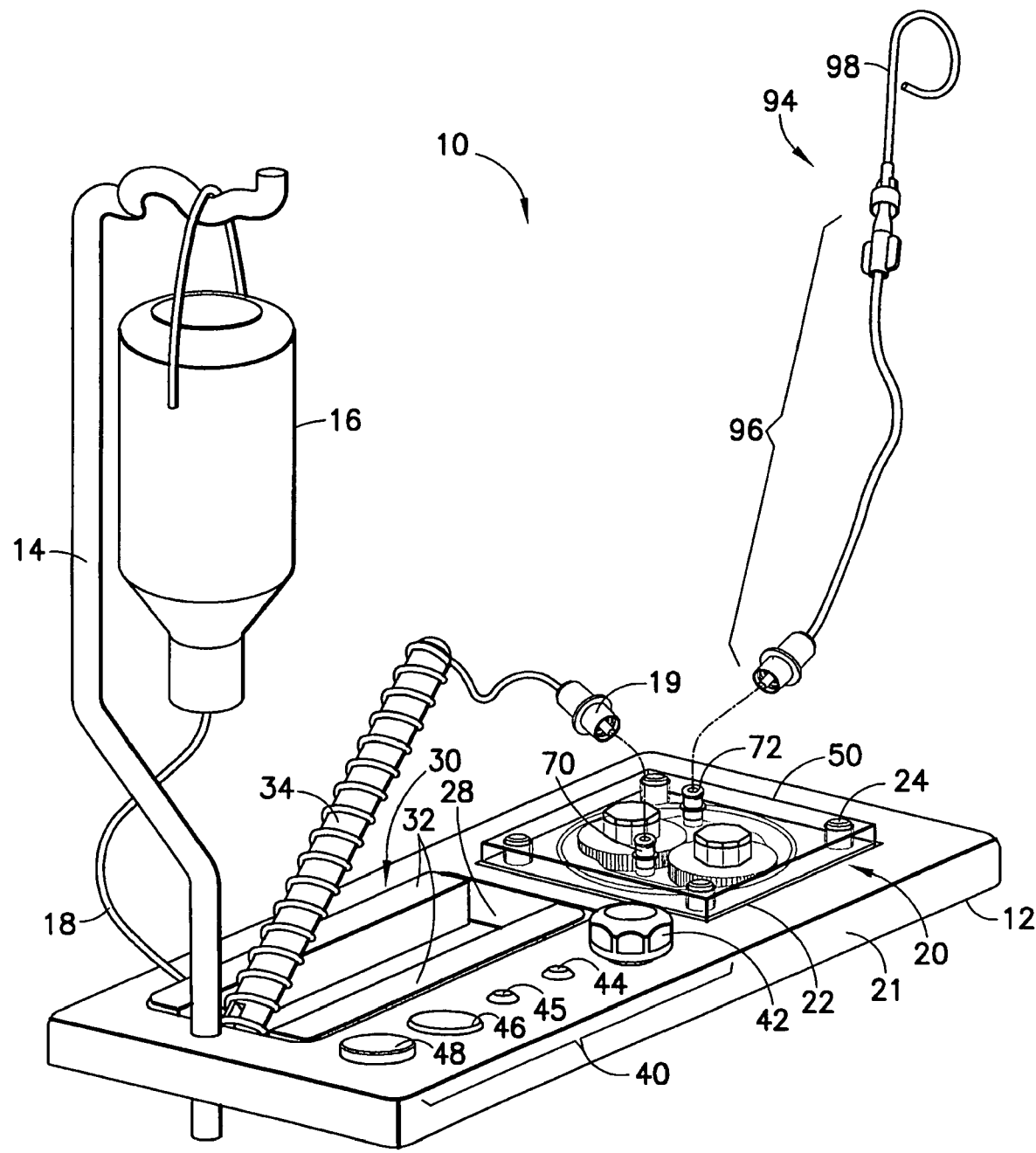
FIG. 6 is a perspective view of the fluid delivery system of FIG. 1 showing a tubing management element associated with a fluid heating section of the control console in a pivoted position.

FIGS. 1 and 6 generally show the overall fluid delivery system 10 including pump cassette 50. As described previously, medical fluid source 16 is typically a bottle or other similar container, such as an intravenous fluid bag (i.e., traditional IV bag), which contains a medical fluid to be delivered to a patient. Medical fluid source 16 is supported on support 14 associated with control console 12 and may contain a load cell (not shown) disposed at the bottom of the medical fluid source 16 (i.e., at the bottom of the supply bottle or IV bag holder) to continuously weigh the contents of the medical fluid source 16. Such a load cell may be linked, for example, wirelessly, to control console 12, and the control console 12 may be adapted to inform a user of system 10 if insufficient fluid is left in the medical fluid source 16 to perform the desired fluid delivery procedure. Medical tubing 18 is connected to medical fluid source 16 and is used to conduct the contents of medical fluid source 16 to pump cassette 50. As shown in FIGS. 1 and 6, fluid heating section 30 on control console 12 is disposed generally between medical fluid source 16 and pump cassette 50 and is used to heat the medical fluid supplied to the pump cassette 50 and, further, as a tubing management apparatus. Such heating of medical fluid, for example, contrast media in the case of CT or CV applications, is primarily for patient comfort but also desirably decreases the viscosity of the contrast media and thereby increases the speed at which the contrast media may be passed through medical tubing 18 and pump cassette 50 for ultimate delivery to a patient.

The heating of medical fluid in fluid heating section 30 on control console 12 may be accomplished in a number of different arrangements on control console 12. Fluid heating section 30 is an example of an apparatus that may be used to heat the medical fluid prior to delivery to a patient. Fluid heating section 30 includes a pair of heating blocks or elements 32 disposed in open recessed area or space 28 defined in control console body 21 of control console 12. Heating elements 32 are desirably laterally disposed on opposing sides of a tubing management element 34 around which medical tubing 18 is wound. The tubing management element 34 may itself be a heating element for heating the medical fluid within medical tubing 18. Typically, tubing management element 34 is used to accommodate and support coiled or spiraled medical tubing 18. As shown in FIG. 6, the tubing management element 34 may be pivotally connected to control console body 21 within recessed area or space 28 so that coiled medical tubing 18 may be easily inserted over the tubing management element 34. Once medical tubing 18 is in place around tubing management element 34, the tubing management element 34 may be pivoted into a position disposed between heating elements 32 so that medical fluid within medical tubing 18 may be heated.

As indicated previously, medical tubing 18 may terminate at one end with terminal or distal end luer connector 19 which is adapted to engage inlet port 70 on second housing member 54 of pump cassette 50 so that a fluid path is established from medical fluid source 16, through fluid heating section 30 on control console 12, and into pump cassette 50 and, more particularly, into the fluid inlet area 60 of pump chamber 58 of pump cassette 50. As also indicated previously, inlet port 70 is formed as a mating luer connector which is adapted to engage terminal luer connector 19 at the end of medical tubing 18. If desired, heating elements 32 may be adapted to move laterally within space 28 from a generally closed position in which the heating elements 32 may contact or come into close proximity to the medical tubing 18 wound around tubing management element 34, to a laterally spaced position wherein the heating elements 32 are spaced away from the lateral sides of the tubing management element 34 to allow the tubing management element 34 to pivot to a pivoted position as shown in FIG. 6.

Figure 7:
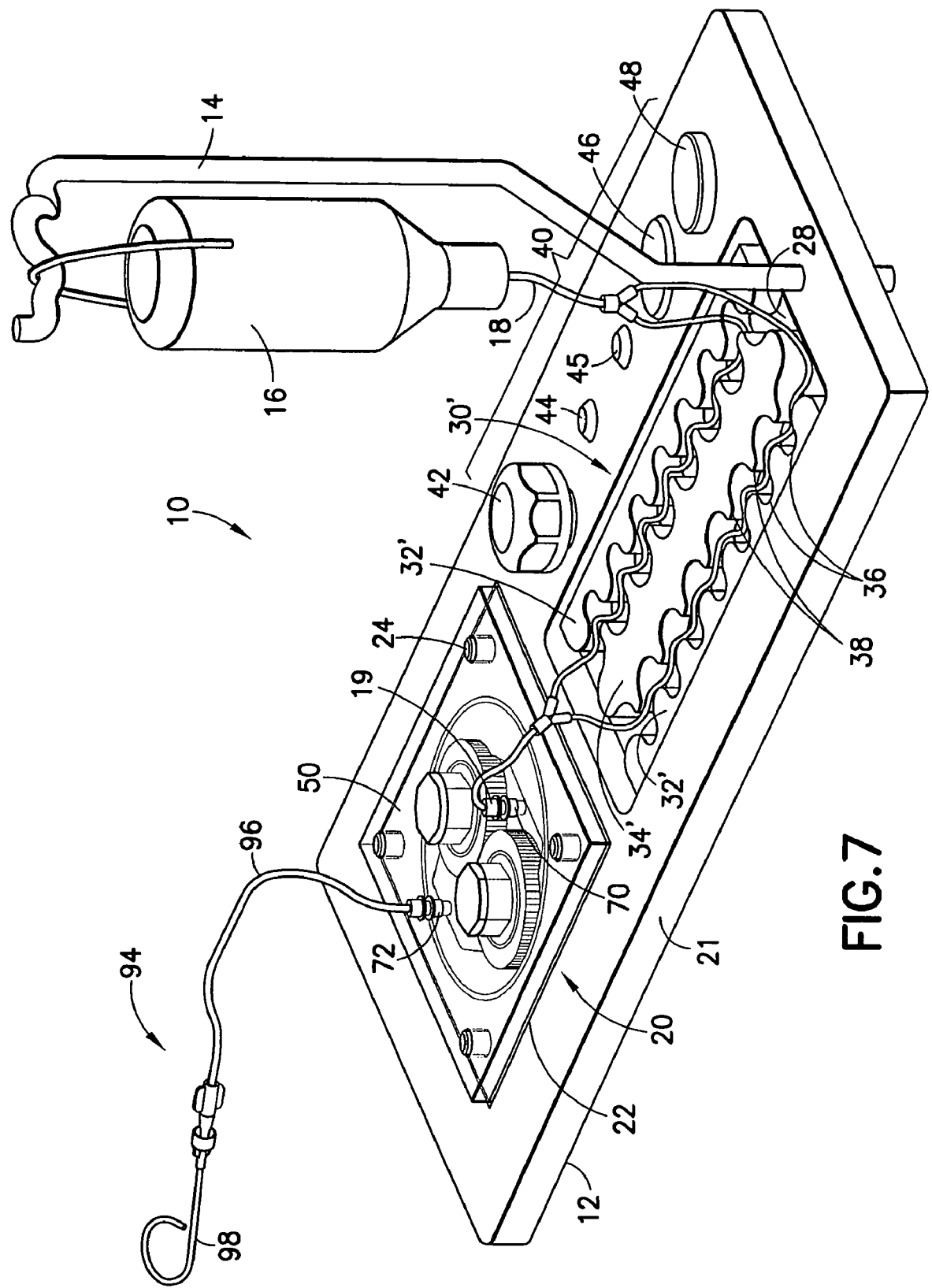
FIG. 7 is a perspective view of the fluid delivery system of FIG. 1 showing another embodiment of the fluid heating section of the control console.

Referring further to FIG. 7, system 10 and control console 12 in particular are shown with a slightly modified fluid heating section 30'. The modified fluid heating section 30' is generally adapted for use with straight, non-coiled medical tubing 18. In FIG. 7, fluid heating section 30' includes the same structures as that shown in FIGS. 1 and 6. However, heating elements 32' and tubing management element 34' are formed to define parallel and generally serpentine paths though the fluid heating section 30' for medical tubing 18. As shown in FIG. 7, heating elements 32' define a series of concave recesses 36 and the tubing management element 34' includes opposing and generally mating convex tabs 38 on lateral sides thereof. Mating convex tabs 38 are formed and are generally located to at least partially engage or register with the concave recesses 36 defined in heating elements 32'. As described previously in connection with FIGS. 1 and 6, heating elements 32 are desirably movable laterally within space 28 so that the heating elements 32 may be moved into close proximity to or contact medical tubing 18 associated with tubing management element 34 for heating purposes and then moved away from the lateral sides of the tubing management element 34 to allow for pivoted movement of the tubing management element 34.

In the embodiment of fluid heating section 30' shown in FIG. 7, tubing management element 34' typically occupies a generally fixed or stationary position within space 28 and the heating elements 32' may be moved laterally towards the tubing management element 34' to bend medical tubing 18 into a serpentine configuration within fluid heating section 30' and, further, to effect heating of the medical fluid carried by the medical tubing 18. Accordingly, as will be appreciated from viewing FIG. 7, when heating elements 32' are moved laterally towards the opposing sides of tubing management element 34', convex tabs 38 cause medical tubing 18, which extends along the opposing sides of tubing management element 34', to be bent into a serpentine. This serpentine configuration increases the length of medical tubing 18 that will be exposed to heating over a straight-line pass through of medical tubing 18 through the fluid heating section 30' on control console 12. To maximize the heating effect, medical tubing 18 ideally splits downstream of medical fluid source 16 and forms two fluid paths through fluid heating section 30', as illustrated in FIG. 7. After exiting fluid heating section 30', the dual track flow path may be rejoined before entering pump cassette 50. Medical tubing 18 may include Y-connectors to effectuate the split flow path through fluid heating section 30' and the rejoined singular flow path downstream of fluid heating section 30'. If desired, medical tubing 18 may define two separate flow paths from medical fluid source 16 and through fluid heating section 30' until rejoining downstream of fluid heating section 30'. Alternatively, the two separate flow paths may be maintained through fluid heating section 30' and each be connected to separate luer connectors, for example, forming two inlet ports 70 on pump cassette 50, as described herein in connection with FIG. 16.

As an alternative to the foregoing embodiments of fluid heating section 30, 30' heating of the medical fluid may be accomplished directly at medical fluid source 16, such as by providing a bottle or bag heater apparatus around the bottle or IV bag containing the medical fluid and forming the medical fluid source 16. Another alternative method of heating medical fluid in system 10 includes incorporating a heating element or device in pump cassette 50. For example, such a heating element or device may be incorporated into the first housing member 52 or second housing member 54 of pump cassette 50, or even as part of gears 56, for example, as part of the gear core 74 or radial casing 78 of each gear 56.

Medical tubing 18 may include a conventional spike connector at a proximal end for engaging the bottle or IV bag forming medical fluid source 16. As indicated previously, terminal or distal luer connector 19 is typically adapted to engage a luer connector forming the inlet port 70 of pump cassette 50. Suitable luer connectors for use in making the fluid connection between inlet port 70 and terminal luer connector 19 and, further, between outlet port 72 and patient interface device 94 may be found in U.S. Patent Application No. 60/741,146, filed Dec. 1, 2005 and entitled "Fluid Deliver System, Fluid Path, and Medical Connector for Use with the Fluid Deliver System and Fluid Path". The disclosure of U.S. Provisional Patent Application No. 60/741,146 is incorporated herein by reference in its entirety.

The patient interface device or section 94 generally includes a medical connector section 96 adapted to engage outlet port 72 on pump cassette 50 and which is further adapted for connection to a fluid delivery implement or device 98, such as a catheter, used to intravenously deliver medical fluid under pressure from pump cassette 50 to a patient. A catheter is only intended as an example of a device which may inserted into a vein or artery of a patient to deliver the medical fluid to the patient. A suitable connector section for medical connector section 96 and a suitable catheter for use as fluid delivery implement or device 98 is disclosed in U.S. Provisional Patent Application No. 60/741,146 incorporated by reference hereinabove.

Control section 40 of control console 12 is adapted to enable a user, typically a medical practitioner, to operate pump cassette 50 to deliver medical fluid from medical fluid source 16 to a patient via the patient interface device or section 94. Control section 40 may include safety features used to prepare the system 10 for use in a fluid delivery procedure or to stop operation of pump cassette 50 in the event a safety hazard is identified by the user of control console 12 or detected by sensors associated with the control console 12, as described herein. The following control elements associated with control section 40 are not intended to be an exhaustive listing and should not be read as limiting the scope of the invention defined by the appended claims. Proceeding from top to bottom in the control section 40 shown, for example, in FIGS. 1 and 6, a manually-operated knob 42 is provided to enable a user of control console 12 to advance fluid through system 10 and to perform patency checks, typically relating to looking for obstructions in the system 10 which will prevent proper operation of pump cassette 50 in a fluid delivery procedure. An auto-prime button 44 and an air-check button 45 are provided next in control section 40.

Figure 8:
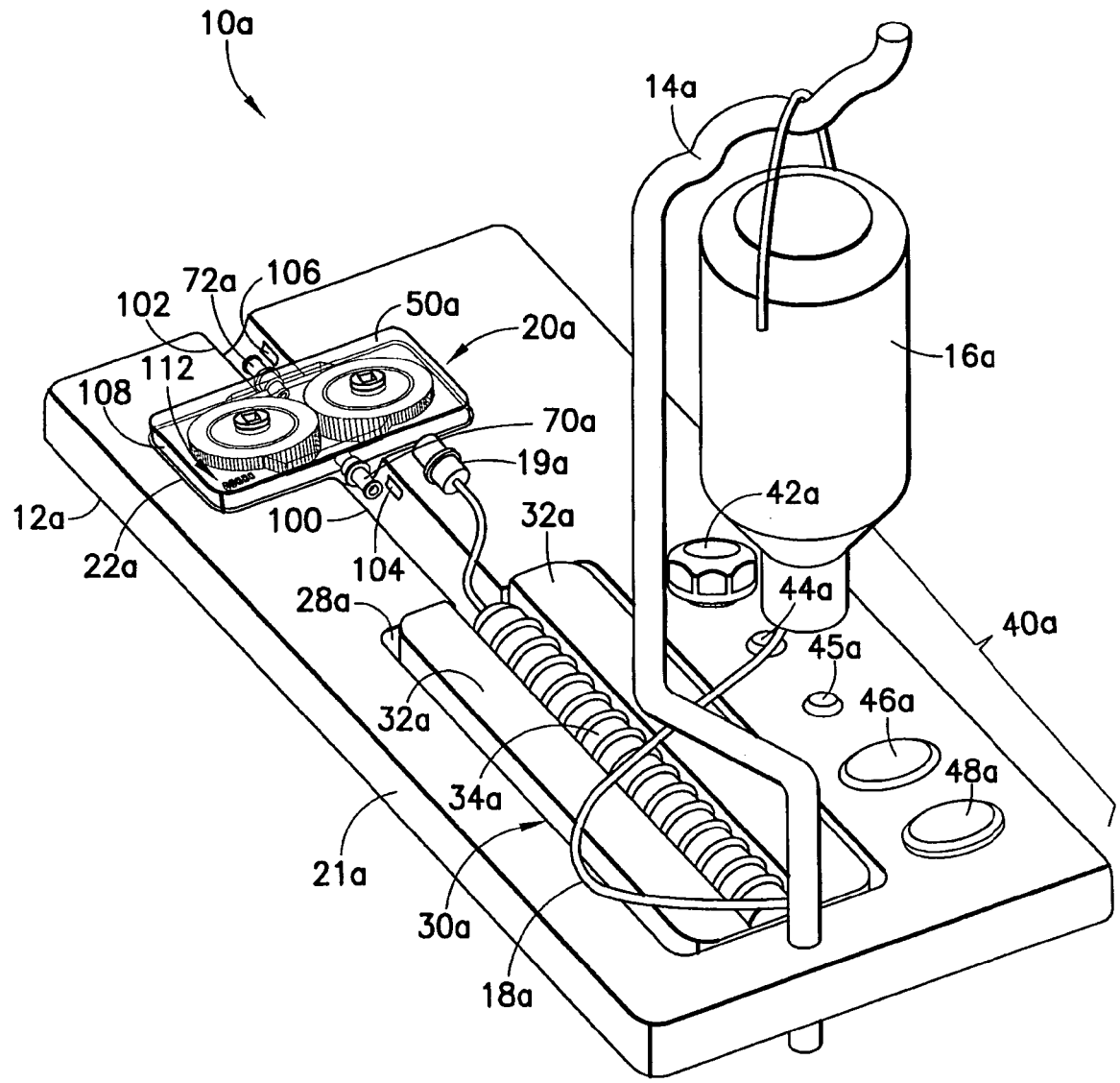
FIG. 8 is a perspective view of another embodiment of the fluid delivery system.
Figure 9:
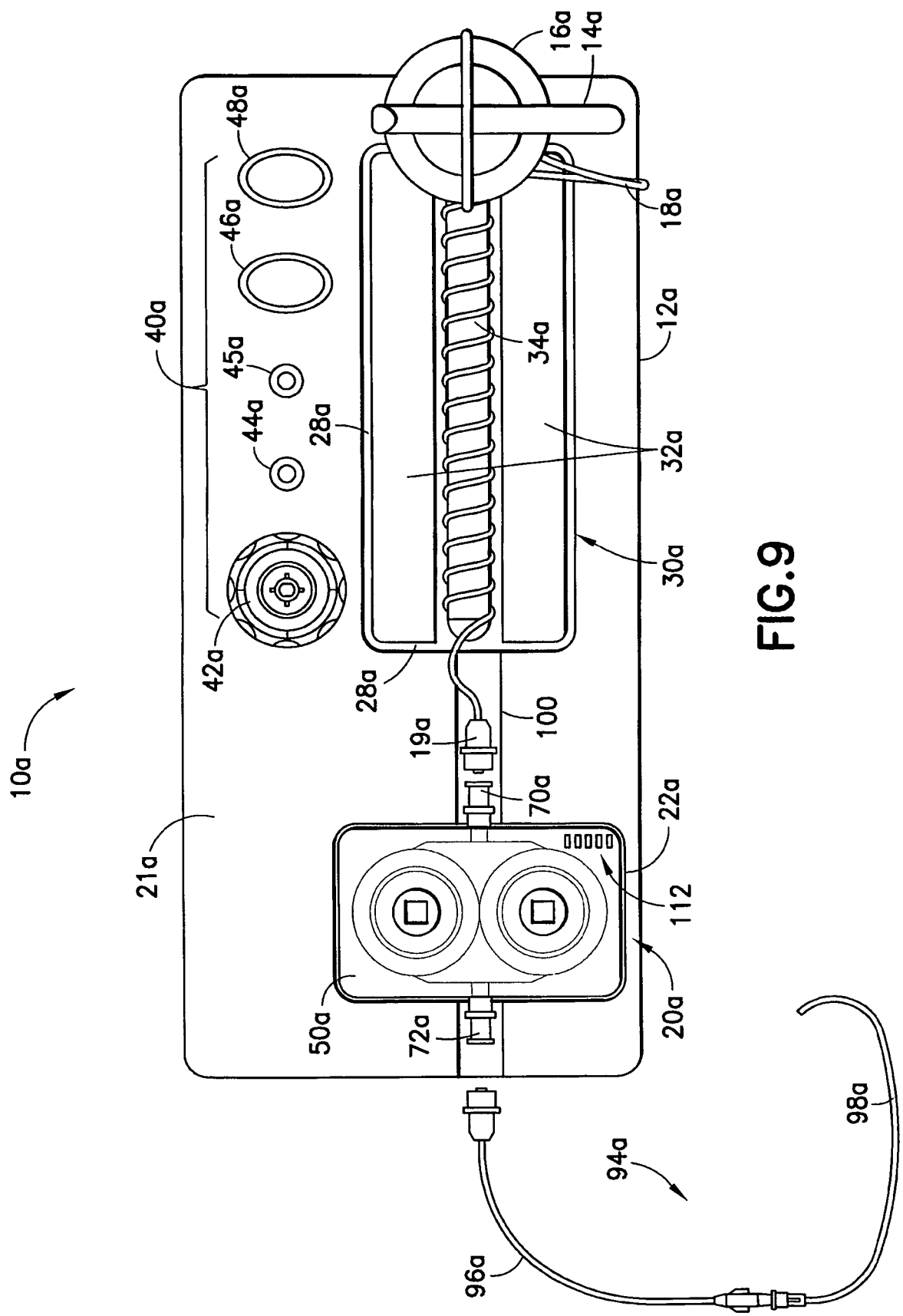
FIG. 9 is a top view of the fluid delivery system of FIG. 8.

Auto-prime button 44 is used to prime system 10 with medical fluid thereby purging air from a system fluid path generally defined by medical tubing 18, pump chamber 58, and patient interface device or section 94. Air-check button 45 is adapted to actuate air detector sensors, discussed herein in connection with FIGS. 8-10, disposed at strategic locations along the system fluid path to determine whether air is present at these locations during operation of the system 10 which could create a hazardous condition if injected into a patient. After the auto-prime button 44 and air-check button 45, a start or actuation button 46 is provided which activates pump cassette 50 to supply medical fluid to a patient. Actuation button 46 may be configured to operate pump cassette 50 to deliver fluid as long as it is depressed, or control console 12 may be provided with an internal control apparatus or device (not shown) such as a microprocessor, for example, which may be programmable to, for example, execute a fluid delivery/injection protocol unique to the patient connected to system 10 via patient interface device 94. Depression of actuation button 46 may be used to initiate the injection protocol which is controlled by the internal control device. It will be appreciated that an external control device may also be used as a control device for control console 12 (as in FIG. 15 discussed herein).

Another example of a control element or button that may be provided on control console 12 in operator control section 40 is an emergency stop button 48 which causes operation of pump cassette 50 to cease substantially immediately when actuated. Such an emergency stop button 48 is typically intended for use by attending medical practitioner operators of system 10 and control console 12. However, an emergency stop of system 10 is not intended to be limited to a manual interrupt of the operation of pump cassette 50 via the actuation of emergency stop button 48 and may be initiated by the internal control device within control console 12. For example, should an air detector sensor associated with control console 12 detect the presence of air in the system fluid path leading from medical fluid source 16 to the patient, a signal may be sent to the internal control device (or external control device) which is interpreted by the internal control device and used to cease operation of pump cassette 50 and interrupt an on-going injection protocol for safety reasons.

Referring now to FIGS. 8-13 another embodiment of system 10a and pump cassette 50a is shown. System 10a comprises the same components as system 10 described previously, with certain modifications to control console 12a and pump cassette 50a. Accordingly, only these specific changes and/or additions to control console 12a and pump cassette 50a are discussed hereinafter as the remaining components of system 10a are identical to system 10 described previously. In system 10a, the control console body 21a of control console 12a defines an inlet passageway 100 extending from fluid heating section 30a to pump cassette 50a. Medical tubing 18a extends through inlet passageway 100 with terminal luer connector 19a connected to inlet port 70a on pump cassette 50a in inlet passageway 100. As shown in detail in FIG. 11, inlet port 70a and outlet port 72a are provided in opposing sidewalls of pump cassette 50 formed by the first and second housing members 52a, 54a of pump cassette 50a rather than in the second housing member 54a as in the embodiment of pump cassette 50 discussed previously. Outlet port 72a is disposed in an outlet passageway 102 defined in control console body 21a and patient interface device 94a is connected to outlet port 72a in outlet passageway 102 to connect pump cassette 50a to the patient interface device 94a.

As mentioned previously, it is desirable to monitor the system fluid path between medical fluid source 16a, pump chamber 58a, and patient interface device 94a for the presence of air in the system fluid path. In one exemplary configuration, air detector sensors 104, 106 are provided in inlet passageway 100 and outlet passageway 102, respectively, to monitor for the presence of air in medical tubing 18a, and/or inlet port 70a disposed in inlet passageway 100, and/or pump outlet 74a disposed in outlet passageway 102. Air detector sensors 104, 106 may be optical or acoustic air detectors and are desirably connected to the internal control device within control console 12a. As a result, an air detection signal sent by air detector sensors 104, 106 may be used as a basis to interrupt operation of pump cassette 50a to prevent the injection of air bubbles into a patient. As is known, optical air detector sensors are designed to sense when air is present in plastic medical tubing, for example, because air to plastic has a higher light reflectivity index than does liquid to plastic.

Control console body 21a defines pump cassette socket 22a of pump cassette interface section 20a on control console 12a in a similar manner to that described previously. Pump cassette socket 22a is adapted to receive pump cassette 50a to operatively associate the pump cassette 50a with the control console 12a in the manner described previously. Thus, pump cassette socket 22a is desirably shaped and sized to match the shape and size of pump cassette 50a. A further feature of the pump cassette interface section 20a on control console 12a in system 10a is the presence of a pump cassette sensor 110 in pump cassette socket 22a. Pump cassette sensor 110 is generally adapted to read a corresponding encoding device 112 on the pump cassette 50a. As a result, control console 12a is able to detect both the presence of pump cassette 50a in pump cassette socket 22a but is also able "read" pump cassette 50a to obtain certain information concerning pump cassette 50a and transmit this information ideally to the on-board internal control device in control console 12a. This information may be used as programming input to the control device which will thereafter direct system 10a to perform a fluid delivery/injection procedure in accordance with the detected information. In this instance, encoding device 112 on pump cassette 50a is a series of indented (i.e., recessed) spaced bars 112a-112e of varying indentation provided in first housing member 52a and, ideally, on second housing member 54a as explained further herein. Spaced bars 112a-112e may be replaced by a bar code as an equivalent encoding device.

Typically, pump cassette sensor 110 is an optical sensor and the first and second housing members 52a, 54a are desirably formed of clear or slightly opaque molded plastic material so that spaced bars 112a-112e may be optically sensed or read by pump cassette sensor 110. Pump cassette sensor 110 is positioned in pump cassette socket 22a to read spaced bars 112a-112e. Accordingly, when pump cassette 50a is inserted into pump cassette socket 22a, pump cassette sensor 110 "reads" encoding device 112 and sends a signal to the control device within control console 12a (or located elsewhere) which then recognizes the presence of pump cassette 50a and, desirably, further interprets the information contained in the signal to modify operation of pump cassette 50a accordingly. Examples of pump cassette information which could be encoded in encoding device 112 include dimensions of pump cassette 50a, recommended flow rate information of pump cassette 50a, for example, minimum and maximum recommended flow rates, manufacturing information such as lot numbers, dates and tool cavity number and, as indicated previously, information used by the internal control device in control console 12a to cause the control console 12a to operate pump cassette 50a in a predetermined manner. For example, the pump cassette information obtained from encoding device 112 could include recommended contrast media flow rates and pressures to be delivered by pump cassette 50a in the case of a CT or CV procedure. As an alternative to encoding device 112 being a series of indented spaced bars 112a-112e, encoding device 112 could also include raised surfaces corresponding to the spaced bars 112a-112e or be a simple bar code, as indicated previously. Encoding device 112 could also be a mechanically read device, such as a slot, hole, or projection on pump cassette 50a which registers with a switch or other electromechanical structure provided in place of pump cassette sensor 110 in pump cassette socket 22a. Another alternative is to provide encoding device 112 as an optically readable device, such as characters, dots, geometric shapes that may be read optically in generally the same manner by pump cassette sensor 110 as the indented spaced bars 112a-112e and which will send information concerning the type of pump cassette 50a being present to the internal control device within control console 12a. Control device 12a may alternatively be controlled by a computer or control device located remotely from the control console 12a, as described herein. Moreover, it will be clear that air detector sensors 104, 106 and pump cassette sensor 110 may be used in system 10 described previously in generally the same manner as set forth hereinabove.

Pump cassette 50a used in system 10a and in conjunction with control console 12a is substantially similar to the embodiment of pump cassette 50 discussed previously, with the additional feature that top and bottom sides or faces 116, 118 of pump cassette 50a may be mirror images so that the pump cassette 50a may be inserted into the pump cassette socket 22a with either top face 116 of pump cassette 50a or bottom face 118 of pump cassette 50a facing downward into pump cassette socket 22a. As a result, first and second housing members 52a, 54a of pump cassette 50a are mirror images of each other, and have generally similar thicknesses, shapes, and each define a portion of pump chamber 58a so that, when joined, the pump chamber 58a is defined between the first and second housing members 52a, 54a. Inlet port 70a and outlet port 72a extend through the respective opposing sidewalls of pump cassette 50a defined or formed by the cooperative engagement of the first and second housing members 52a, 54a. First and second housing members 52a, 54a are secured together with, for example, by a suitable medical grade adhesive with the perimeter seal 64 discussed previously in connection with pump cassette 50 omitted. The desired fluid seal about pump chamber 58a is provided by the adhesive connection between the first and second housing members 52a, 54a, obviating the need for perimeter seal 64 described previously. Since pump cassette 50a may be inserted in pump cassette socket 22a with either face 116, 118 facing downward, both the first housing member 52a and the second housing member 54a are desirably provided with an encoding device 112.

Further, since either face 116, 118 of pump cassette 50a may be inserted into pump cassette socket 22a, gears 56a are desirably configured to be driven through either the first housing member 52a or the second housing member 54a. Top and bottom oriented openings 86a, 88a, discussed previously, in connection with pump cassette 50 and shown more completely in FIG. 13 enable the gears 56a in pump cassette 50a to be driven in either the top down or bottom down configuration in pump cassette socket 22a. As described previously, gears 56a include a gear core 74a with identical top and bottom drive element interfaces 78a. In pump cassette 50 described previously, drive element interfaces 78 were adapted to engage socket-type drive elements 26 in the pump cassette interface section 20 on control console 12. In the present embodiment, drive element interfaces 78a are adapted to pass through the respective openings 86a, 88a in the first and second housing members 52a, 54a and engage shaft-type drive elements 26a which are shown in FIG. 10. As shown in FIG. 10, drive elements 26a in the pump cassette interface section 20a on control console 12a are provided as drive shafts which are adapted to be inserted into receiving openings or recesses 120 in drive element interfaces 76a. Since pump cassette 50a is adapted to be driven in either a top face 116 down or bottom face 118 down configuration, receiving openings 120 are provided in both the top and bottom drive element interfaces 76a on each gear core 74a of each gear 76a and may be recesses or a through hole passing entirely through each gear core 74a. Drive elements 26a and gear cores 74a may be constructed in the manner of drive element interfaces 76 and drive elements 26 described previously in connection with FIGS. 1-6.

Figure 14A:
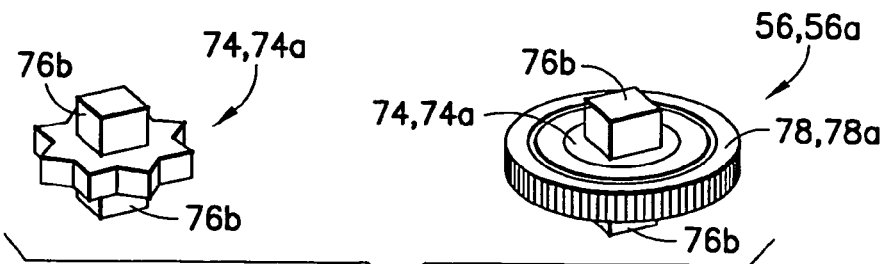
FIGS. 14A-14E are perspective views illustrating alternative gear embodiments adapted for use in the pump cassette of FIG. 11.
Figure 14B:
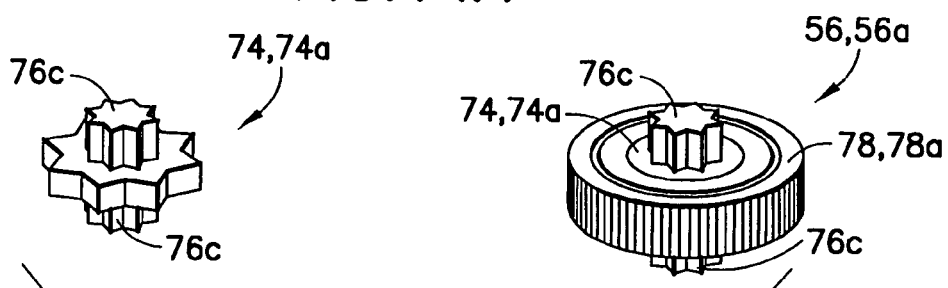
Figure 14C:
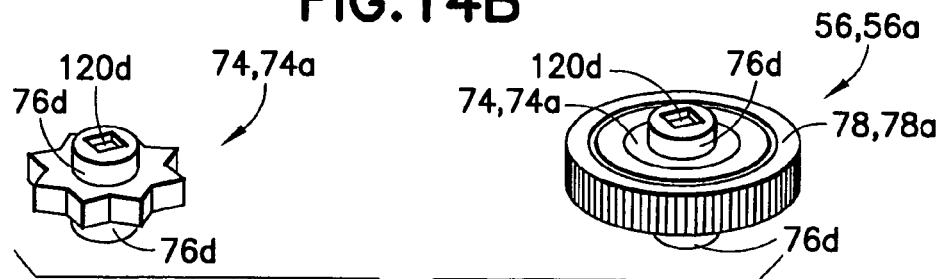
Figure 14D:
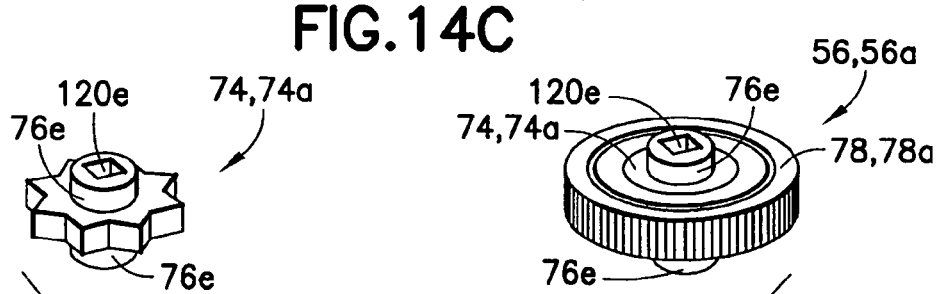
Figure 14E:

In the foregoing, gears 56, 56a were described with gear cores 74, 74a comprising top and bottom extending drive element interfaces 76, 76a which are adapted to engage socket-type drive elements 26 or shaft-type drive elements 26a in the pump cassette socket 22, 22a of the pump cassette interface section 20, 20a on control console 12, 12a. FIGS. 14A-14E illustrates various examples of gears 56, 56a with gear cores 74, 74a comprising various different embodiments of drive element interfaces 76, 76a which are adapted to engage socket-type drive elements similar to drive elements 26 discussed previously in connection with FIG. 2 or shaft-type drive elements such as drive elements 26a discussed previously in connection with FIG. 10. In FIG. 14A, drive element interfaces 76b are shown having a square shape adapted to engage square-shaped socket drive elements similar to the socket drive elements 26 shown in FIG. 2. In FIG. 14B, the drive element interfaces 76c are star-shaped for engaging star-shaped socket drive elements similar to the socket drive elements 26 shown in FIG. 2. In FIGS. 14C-14E, drive element interfaces 76d-f are adapted to engage shaft-type drive elements similar to the shaft drive elements 26a shown in FIG. 10. FIGS. 14C-14E show various embodiments of receiving openings 120d-f in drive element interfaces 76d-f for receiving shaft-type drive elements similar to the shaft drive elements 26a shown in FIG. 10. In FIG. 14C, receiving openings 120d are square-shaped in the same manner as receiving openings 120 discussed previously but are formed as recesses rather than through bores or holes through the gear core 74a. In FIG. 14D, receiving openings 120e are identical to receiving opening 120 described previously. In FIG. 14E, receiving openings 120f are through holes or bores but exhibit a star-shape. As described previously, drive elements 26, 26a may take any mating configuration for engaging drive element interfaces 76, 76a. Moreover, the drive elements 26, 26a and drive element interfaces 76, 76a may have mating circular configurations, with one including a protruding pin or spline and the mating structure defining a groove for accepting the pin or spline for driving gears 56, 56a in pump cassette 50, 50a.

Further, as will be appreciated from viewing FIGS. 10-13 in particular, the mirror image configuration of pump cassette 50a allows the pump cassette 50a to be inserted into pump cassette socket 22a of the pump cassette interface 20a on control console 12a so that inlet port 70a may function as the outlet port for pump cassette 50a and outlet port 72a may function as the inlet port for pump cassette 50a. In such a use, inlet port 70a is aligned with outlet passageway 102 and outlet port 72a is aligned with inlet passageway 100 when pump cassette 50a is inserted into the pump cassette socket 108. Gears 56a may be driven by drive elements 26a in pump cassette socket 22a in either inserted configuration of pump cassette 50a in the manner described previously.

Additional air detector sensors 122, 124 may also be provided in pump cassette socket 22a, for example in the general location of fluid inlet area 60a and fluid outlet area 62a when pump cassette 50a is inserted into pump cassette socket 22a of the pump cassette interface 20a on control console 12a. Such air detector sensors 122, 124 may be optical or acoustic type sensors. As described previously, optical air detector sensors are designed to sense when air is present in a plastic medical device because air to plastic has a higher light reflectivity index than does liquid to plastic. As a result, the first housing member 52a and second housing member 54a are typically formed of clear or slightly opaque molded plastic material so that air detector sensors 122, 124, if provided as optical air detector sensors, may be able to ascertain the presence of air in pump chamber 58a of pump cassette 50a, and send a signal or signals to the internal control device in control console 12a. The ability of air detector sensors 104, 106 and 122, 124 to detect air in inlet and outlet ports 70a, 72a and pump chamber 58a and transmit this information by way of signals the internal control device in control console 12a provides fluid delivery system 10a with the ability to monitor the purging of air from the system fluid path, to stop the purge procedure when all air has been purged from the system fluid path, and not accept a user command to operate the pump cassette 50a if air is present in the system fluid path. Further, fluid delivery system 10a may be adapted such that a positive detection of air by outlet port air detector sensor 106a will initiate a cessation of operation of pump cassette 50a to insure that air is not inadvertently injected into a patient.

Figure 15:
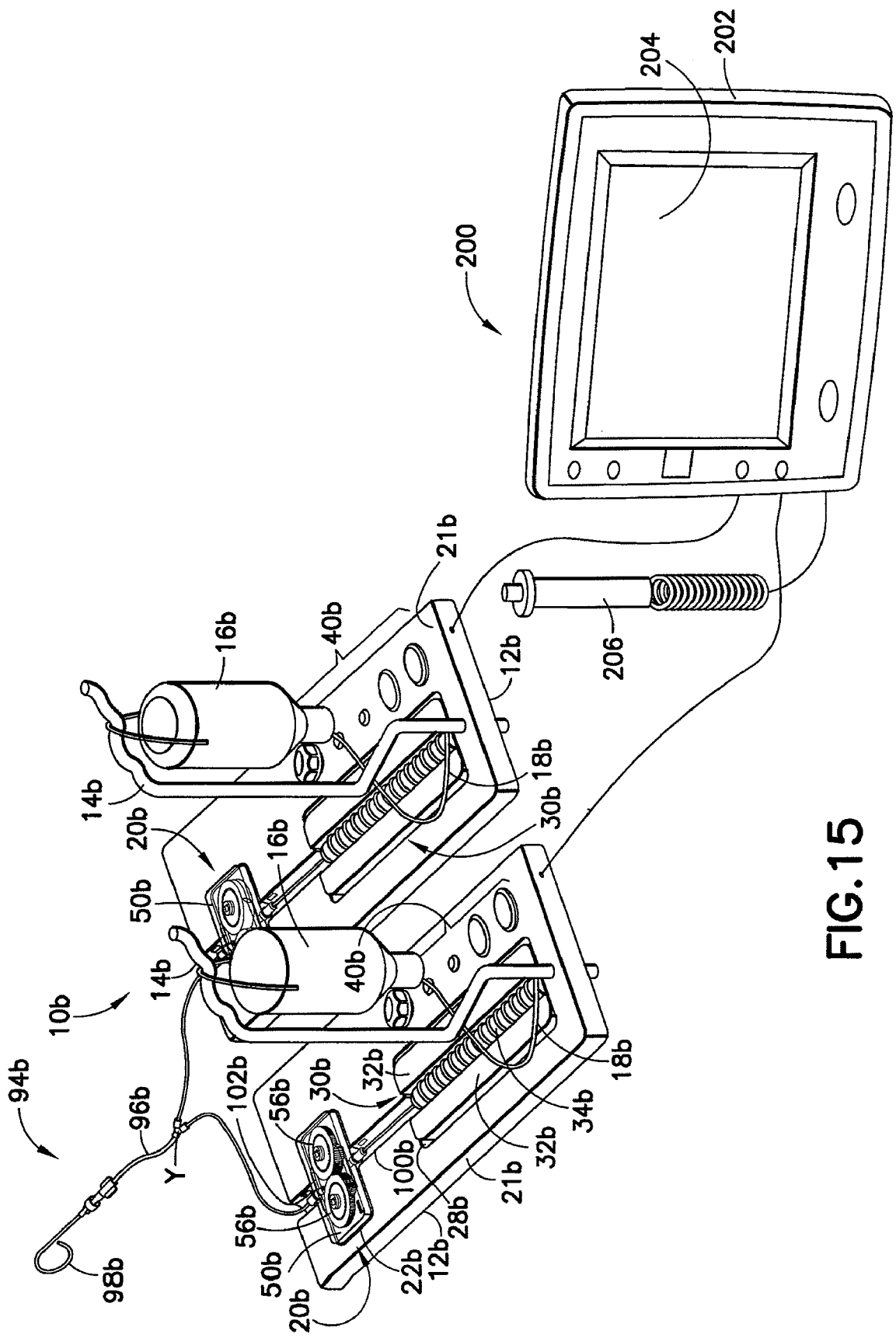
FIG. 15 is a perspective view of a fluid delivery system including two control consoles of the kind illustrated in FIG. 8, for example, and incorporating control elements for controlling operation of the control consoles in the fluid delivery system.

FIG. 15 shows a fluid delivery system 10b with a pair of control consoles 12b operated by an external central control unit 200. Each control console 12b includes a pump cassette 50b fluidly coupled to a medical fluid supply source 16b in the manner described previously. Medical fluid sources 16b may be filed with the same medical fluid or different medical fluids. As shown in FIG. 15 patient interface device 94b is fluidly coupled to both pump cassettes 50b via a Y-connector Y or any equivalent fitting to receive medical fluid from both medical fluid sources 16b. As an example, one medical fluid source 16b may comprise saline and the second medical fluid source 16b may comprise contrast media used in CT and CV applications. Control unit 200 may be adapted to operate the control consoles 12b simultaneously or sequentially to deliver both fluids simultaneously or sequentially to patient interface device 94b. Accordingly, contrast and saline may be provided concurrently to patient interface device 94b, for example, in mixed form via mixing device (not shown) provided in place of Y-connector Y in FIG. 15, or sequentially through alternate operation of the respective control consoles 12b and, thus, alternate operation of pump cassettes 50b associated with the control consoles 12b. Check valves may be associated with Y-connector Y to prevent backflow into the respective conduits connected to the respective pump cassettes 50b when only one is operating. Due to the defined quantity or volume of liquid that is carried by each gear 56b in the respective pump cassettes 50b, operation of the pump cassettes 50b may be controlled differently to achieve downstream fluid mixtures of known ratios at catheter 98b. For example, since saline and contrast media have substantially different fluid viscosities, to achieve a fluid mixture of 50% saline and 50% contrast media at catheter 98b, the pump cassette 50b connected to a contrast media fluid source may be operated at a higher rate (RPM) than the pump cassette 50b connected to a saline fluid source so that equal parts saline and contrast media are mixed in Y-connector Y or another similar mixing device or chamber, such as a static mixer with internal mixing vanes. Control unit 200 may be used to control operation of pump cassettes 50b to achieve this result.

Control unit 200 is typically a computer with programmable memory and comprises a user interface device 202, such as a touch screen 204, for inputting fluid injection protocol information into the memory of control unit 200. In CT and CV applications, such fluid injection protocol information may include: 1) the contrast media concentration desired; 2) the flow rate; and 3) the total volume to be delivered. Control unit 200 may be programmed to determine the necessary flow rate and pressure to be delivered from each pump cassette 50b to meet the desired contrast media concentration, flow rate delivered to the patient, and length of time each pump cassette 50b must operate to deliver the requested total volume of fluid. Touch screen 204 may be used to initiate and, if desired, control the progression of a fluid injection procedure. Such a procedure may be initiated by touching a "start" button on touch screen 204 once all appropriate fluid injection protocol information has been inputted in the memory of control unit 200. Additional control buttons (not shown) may be provided on touch screen 204 to control the fluid injection procedure as it is on-going. Moreover, touch screen 204 desirably displays data from the various sensors associated with each control console 12b to monitor for such hazardous conditions as air bubbles in the system fluid path. Such sensors may provide automatic interrupt signal to control unit 200 which are interpreted by control unit 200 and alerts the control unit 200 to discontinue operation of the respective pump cassettes 50b. As indicated previously, each pump cassette 50b may include an encoding device 112b which is read by the pump cassette sensor 110 (as shown in FIG. 10). The pump cassette information encoded in each encoding device 112b may be used protocol programming inputs to control unit 200. Another user interface device that may be associated with control unit 200 is a handheld controller 206 which is operatively connected to control unit 200 and which may be used to begin a fluid injection procedure or provide user control inputs to control unit 200 to control the fluid injection procedure as it is on-going. While two control consoles 12b are shown in FIG. 15, this just an exemplary configuration and control unit 200 may be used to operate any number of control consoles 12b each operating a pump cassette 50b fluidly coupled to a medical fluid source 16b. It will be appreciated that each medical fluid source 16b may be a different medical fluid which may be administered individually or in various selected combinations and mixtures via patient interface device 94b. It will be further appreciated that multiple patient interface devices 94b may be provided. For example, some of such multiple control consoles 12b may have their pump cassette 50b connected to patient interface device 94b comprising catheter 98b as the fluid delivery implement 98b while others are connected to an IV needle cannula acting as the fluid delivery implement 98b.

Figure 16:
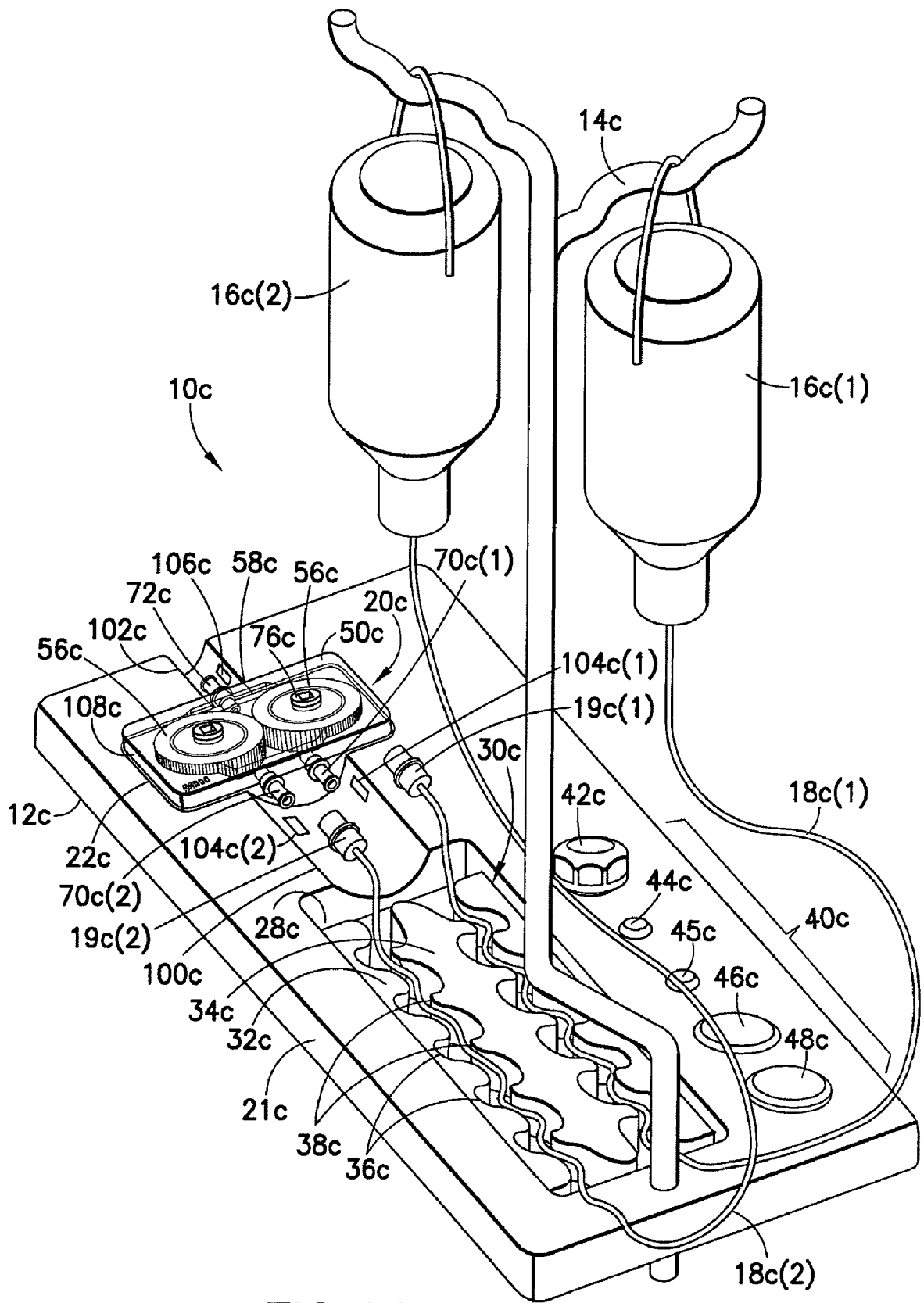
FIG. 16 is a perspective view of another embodiment of the fluid delivery system including a single control console and a pump cassette with two inlet ports for different medical fluids.

FIG. 16 shows a fluid delivery system 10c comprising a single control console 12c which may be operated by external central control unit 200 (shown in FIG. 15), if desired. Control console 12c includes a pump cassette 50c which is fluidly coupled to two or more and typically different medical fluid supply sources 16c(1), 16c(2). However, in contrast to system 10b shown in FIG. 15, pump cassette 50c comprises two inlet ports 70c(1), 70c(1) respectively connected to fluid supply sources 16c(1), 16c(2) via separate medical tubing lines 18c (1), 18c(2) and separate luer connectors 19c(1), 19c(2). Medical fluid sources 16c(1), 16c(2) are typically two different medical fluids, such as contrast media and saline, which are delivered separately to pump cassette 50c and which are mixed in pump chamber 58c by the rotating action of gears 56c. A mixed fluid, for example, diluted contrast media, is delivered to outlet port 72c which may be connected catheter 98b (shown in FIG. 15) to deliver the mixed fluid to a patient intravenously. The rotation of gears 56c in pump chamber 58c provides an advantageous mixing action to the separate fluids delivered to the pump chamber 58c and system 10c is particularly adapted to providing a mixed or diluted fluid to a patient. The respective fluid paths medical fluid sources 16c (1), 16c(2) to pump cassette 50c are heated in fluid heating section 30c which is similar to heating section 30 shown in FIG. 7. However, the separate medical tubing lines 18c(1), 18c(2) connected to medical fluid sources 16c(1), 16c(2) pass separately through fluid heating section 30c along opposing sides of tubing management device 34c, which may be a heating element in its own right if desired as described previously. It is generally desirably in fluid delivery system 10c to use medical fluid sources 16c(1), 16c(2) that contain fluid of similar viscosity. If the medical fluid sources 16c(1), 16c (2) vary significantly in viscosity it may be difficult to control the ratio of fluids mixed by pump cassette 50c due to the differing flow rates of fluid entering pump cassette 50c from the medical fluid sources 16c(1), 16c(2). However, this problem may be compensated for easily by locating the medical fluid sources 16c(1), 16c(2) at different elevations or increasing the flow resistance in or length of medical tubing 18c(1), 18c(2) or a combination of these corrective measures.

Figure 17:
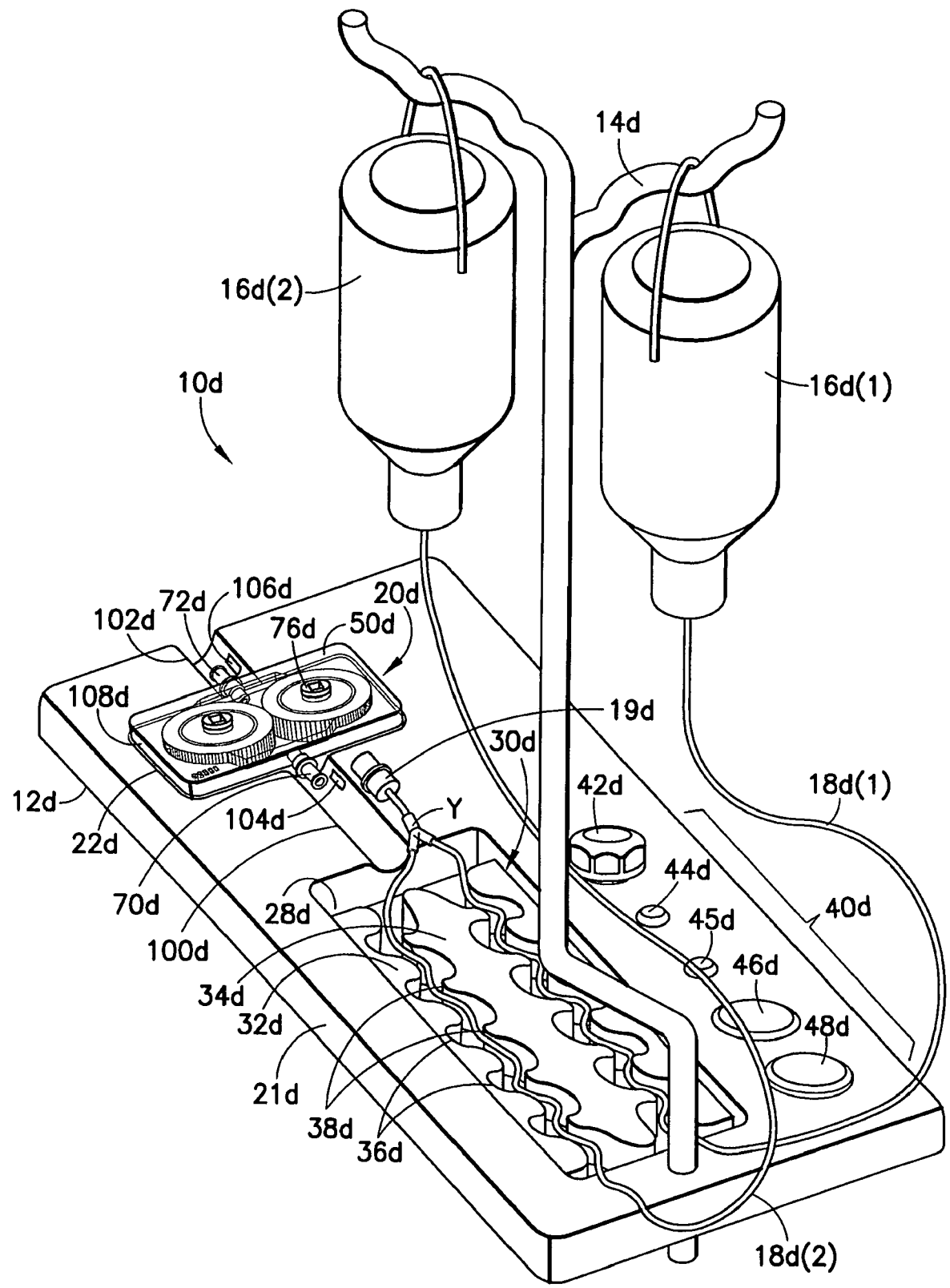
FIG. 17 is a perspective view of a further embodiment of the fluid delivery system including a control console of the kind illustrated in FIG. 8, for example, and a pump cassette adapted to receive a mixture of different medical fluids.

Finally, FIG. 17 shows a further embodiment of fluid delivery system 10d which is generally similar to fluid delivery system 10b discussed previously, with control console 12d including a single pump cassette 50d. However, pump cassette 50d is fluidly coupled to two or more and typically different medical fluid sources 16d(1), 16d(2) in a similar manner to system 10c discussed immediately above. In system 10d shown in FIG. 17, pump cassette 50d comprises a single inlet port 70d and medical fluid sources 16d(1), 16d(2) are connected to inlet port 70d via separate medical tubing lines 18d(1), 18d(2) which are joined by a Y-connector Y. Luer connector 19d is located downstream of Y-connector Y for making the physical connection to inlet port 70d. Fluid heating section 30d is generally similar to fluid heating section 30c discussed immediately above. Y-connector Y, or a similar mixing device or chamber, such as a static mixer with internal mixing vanes, is used to mix the respective fluids from medical fluid sources 16d(1), 16d(2) upstream of pump cassette 50d thus allowing a mixed fluid to enter pump cassette 50d. Operation of pump cassette 50d will cause the medical fluids from medical fluid sources 16d(1), 16d(2) to pass through medical tubing lines 18d(1), 18d(2) at known but different flow rates when these medical fluids have different viscosities. However, a calculation can easily made, for example, by the internal control unit in pump cassette 50d or control unit 200, to determine the ratio of fluids in the mixed fluid entering pump cassette 50d. From this information, it will be known what mixture of fluids is being delivered by pump cassette 50d to a patient. The ratio of fluids in the mixed fluid in pump cassette 50d may be changed by locating the medical fluid sources 16d(1), 16d(2) at different elevations or increasing the flow resistance in or length of medical tubing 18d(1), 18d(2) or a combination of these corrective measures.

While the present invention was described by way of a detailed description of several embodiments of a fluid delivery system and a pump cassette therefor, those skilled in the art may make modifications and alterations to this invention without departing from the scope and spirit of the invention. Accordingly, the foregoing description is intended to be illustrative rather than restrictive. The invention described hereinabove is defined by the appended claims, and all changes to the invention that fall within the meaning and the range of equivalency of the claims are to be embraced within their scope.

The invention claimed is:

1. A pump cassette for delivering fluid to patient, comprising:
   a pump housing comprising a first housing member and a second housing member cooperatively defining an enclosed pump chamber with an interior wall;
   at least a pair of meshed gears disposed in the pump chamber and separating the pump chamber into a fluid inlet area and a fluid outlet area accessible through respective inlet and outlet ports in the pump housing, and
   a gear core disposed on a center of each of the gears and formed symmetrically on a top and a bottom of each gear;
   a drive element interface formed on each of the gear cores;
   wherein the first and second housing members are formed substantially identically such that a top side and the bottom side of the pump housing are substantially identical,
   wherein the first housing member includes top oriented openings and the second housing member includes bottom oriented openings such that each drive element interface is disposed within a corresponding top or bottom oriented opening permitting the gears to be driven from either the top or bottom of the housing whereby fluid is pressurized for delivery to the patient.

2. The pump cassette as claimed in claim 1 wherein each of the gears is in contact with the interior wall over at least a portion of its periphery.

3. The pump cassette as claimed in claim 1 wherein the meshed gears comprise spur gears.

4. The pump cassette as claimed in claim 1 wherein the meshed gears are composite structures each comprising the gear core made of a substantially rigid material and a resiliently deformable radial casing disposed about the gear core.

5. The pump cassette as claimed in claim 1 wherein the inlet port and outlet port are luer connectors.

6. The pump cassette as claimed in claim 1 further comprising an encoding device associated with the pump housing and operable to provide pump cassette information to a sensor.

7. The pump cassette as claimed in claim 6 wherein the encoding device comprises an optically readable device.

8. The pump cassette as claimed in claim 6 wherein the pump cassette information is selected from the group consisting of pump cassette sizing information, pump cassette flow rate information, and pump cassette manufacturing information.

9. The pump cassette as claimed in claim 1 wherein at least an outer periphery of each gear is resiliently deformable.

10. The pump cassette as claimed in claim 1 wherein the spacing between gear teeth on each gear is sized to conduct a predetermined amount of fluid about the periphery of the gear along the interior wall.

11. A fluid delivery system, comprising:
    a control console; and
    a pump cassette connected to and operated by the control console for delivering fluid to a patient, the pump cassette comprising:
    a pump housing comprising a first housing member and a second housing member cooperatively defining an enclosed pump chamber with an interior wall; and
    at least a pair of meshed gears disposed in the pump chamber and separating the pump chamber into a fluid inlet area and a fluid outlet area accessible through respective inlet and outlet ports in the pump housing, and adapted to pressurize fluid for delivery to the patient,
    a gear core disposed on a center of each meshed gear;
    a drive element interface formed on each of the gear cores;
    wherein the first and second housing members are formed substantially identically such that a top side and a bottom side of the pump housing are symmetric,
    wherein the first housing member includes top oriented openings and the second housing member includes bottom oriented openings such that each drive element interface is disposed within the a corresponding top or bottom oriented opening permitting the gears to be driven from either the top or bottom of the housing whereby fluid is pressurized for delivery to the patient.

12. The fluid delivery system as claimed in claim 11 wherein the pump cassette is disposed in a pump cassette socket in the control console.

13. The fluid delivery system as claimed in claim 11 wherein the control console further comprises a fluid heater upstream of the pump cassette to provide heated fluid to the pump chamber.

14. The fluid delivery system as claimed in claim 11 wherein the control console further comprises an air detector associated with the inlet port and/or outlet port of the pump housing.

15. The fluid delivery system as claimed in claim 11 wherein the control console comprises a sensor adapted to detect an encoding device associated with the pump housing and operable to provide pump cassette information to the sensor.

16. The fluid delivery system as claimed in claim 15 wherein the encoding device comprises an optically readable device.

17. The fluid delivery system as claimed in claim 15 wherein the pump cassette information is selected from the group consisting of pump cassette sizing information, pump cassette flow rate information, and pump cassette manufacturing information.

18. The fluid delivery system as claimed in claim 11 wherein each of the gears is in contact with the interior wall over at least a portion of its periphery.

19. The fluid delivery system as claimed in claim 11 wherein the inlet port and outlet port are luer connectors.

20. The fluid delivery system as claimed in claim 11 wherein the meshed gears are composite structures each comprising the gear core made of a substantially rigid material and a resiliently deformable radial casing disposed about the gear core.

21. The fluid delivery system as claimed in claim 11 wherein at least an outer periphery of each gear is resiliently deformable.

22. The fluid delivery system as claimed in claim 11 wherein the spacing between gear teeth on each gear is sized to conduct a predetermined amount of fluid about the periphery of the gear along the interior wall of the pump chamber.

23. A method of preparing a fluid delivery system to provide fluid to a patient, comprising:
    providing a control console adapted to control delivery of fluid to the patient;
    operatively associating a pump cassette with the control console, the pump cassette comprising:
    a pump housing defining an enclosed pump chamber; and
    at least a pair of meshed gears disposed in the pump chamber and separating the pump chamber into a fluid inlet area and a fluid outlet area accessible through respective inlet and outlet ports in the pump housing, wherein the control console is adapted to control operation of the pump cassette for delivering fluid to the patient; and a gear core disposed on a center of each meshed gear;

a drive element interface formed on each of the gear cores;

wherein the pump housing includes first and second housing members formed substantially identically such that opposing sides of the pump housing are substantially identical, wherein the first housing member includes top oriented openings and the second housing member includes bottom oriented openings such that each drive element interface is disposed within a corresponding top or bottom oriented opening permitting the gears to be driven from either the top or bottom of the housing whereby fluid is pressurized for delivery to the patient; and placing the pump chamber in fluid communication with a source of fluid to be delivered to the patient.

24. The method as claimed in claim 23 further comprising heating the fluid upstream of the pump cassette.

25. The method as claimed in claim 23 further comprising monitoring the inlet port and/or outlet port for the presence of air bubbles.

26. The method as claimed in claim 23 further comprising sensing an encoding device on the pump housing with a sensor on the control console, the encoding device adapted to provide pump cassette information to the sensor.

27. The method as claimed in claim 26 wherein the encoding device is optically sensed.

28. The method as claimed in claim 26 wherein the control console controls operation of the pump cassette based on the pump cassette information sensed from the encoding device.

29. The method as claimed in claim 23 further comprising connecting the control console to a user interface device adapted to input one or more fluid delivery parameters to the control console.

30. The method as claimed in claim 29 wherein the user interface device is further adapted to control operation of the pump cassette upon actuation.

* * * * *

UNITED STATES PATENT AND TRADEMARK OFFICE
CERTIFICATE OF CORRECTION

PATENT NO. : 7,618,397 B2  Page 1 of 1
APPLICATION NO. : 11/403119
DATED : November 17, 2009
INVENTOR(S) : Jeffery H. Hicks It is certified that error appears in the above-identified patent and that said Letters Patent is hereby corrected as shown below:

ON THE TITLE PAGE
In Item (56), under "OTHER PUBLICATIONS", in Column 2, Line 1,
delete "Internationlal" and insert -- International --, therefor.

IN THE SPECIFICATION
In Column 6, Line 29, delete "will" and insert -- with --, therefor.

IN THE CLAIMS
In Column 22, Line 12, in Claim 11, delete "the a" and insert -- the --, therefor.

Signed and Sealed this

Seventeenth Day of August, 2010

David J. Kappos
*Director of the United States Patent and Trademark Office*